United States Patent [19]
Kramer et al.

[11] Patent Number: 5,916,167
[45] Date of Patent: Jun. 29, 1999

[54] SURGICAL PROBE APPARATUS AND SYSTEM

[75] Inventors: Daniel A. Kramer, Dublin; Beth Ann Kizer; William G. Atterbury, both of Columbus; Marty J. Warnecke, Grandview, all of Ohio; Steve W. Stracener, Frederick, Colo.; Jan B. Yates, Reynoldsburg, Ohio

[73] Assignee: Neoprobe Corporation, Columbus, Ohio

[21] Appl. No.: 08/949,125

[22] Filed: Oct. 10, 1997

[51] Int. Cl.$^6$ ........................................................ A61B 5/00
[52] U.S. Cl. .................. 600/436; 250/370.11; 250/336.1
[58] Field of Search ..................................... 600/436, 407; 250/336.1, 370.13, 370.11

[56] References Cited

U.S. PATENT DOCUMENTS

| | | |
|---|---|---|
| D. 390,480 | 2/1998 | Atterbury et al. . |
| D. 390,481 | 2/1998 | Atterbury et al. . |
| D. 390,485 | 2/1998 | Atterbury et al. . |
| 3,669,095 | 6/1972 | Kobayashi et al. . |
| 4,243,884 | 1/1981 | Avera, Jr. . |
| 4,893,013 | 1/1990 | Denen et al. . |
| 5,036,201 | 7/1991 | Carroll et al. . |
| 5,070,878 | 12/1991 | Denen . |
| 5,119,818 | 6/1992 | Carroll et al. . |
| 5,151,598 | 9/1992 | Denen . |
| 5,166,073 | 11/1992 | Lefkowitz et al. . |
| 5,170,055 | 12/1992 | Carroll et al. . |
| 5,475,219 | 12/1995 | Olson . |
| 5,682,888 | 11/1997 | Olson et al. . |
| 5,694,933 | 12/1997 | Madden et al. . |
| 5,732,704 | 3/1998 | Thurston et al. . |

*Primary Examiner*—Marvin M. Lateef
*Assistant Examiner*—Shawna J. Shaw
*Attorney, Agent, or Firm*—Mueller & Smith, L.P.A.

[57] ABSTRACT

A surgical probe wherein a heat sterilizable and reusable detector component is combined with a disposable handle and cable assembly. The reusable detector component incorporates a detector crystal and associated mountings along with preamplifier components. It is formed having a positioning shaft extending therefrom to a contact supporting surface carrying a pattern of electrical contact surfaces. Two orientation bosses are formed with the positioning shaft. The disposable handle employs an insert member having a receiving cavity. The electrical contact carrying tip of the shaft engages an elastomeric seal and moves into electrical engagement with a pattern of electrical contacts mounted within the handle in conjunction with a permanently affixed flexible cable.

32 Claims, 20 Drawing Sheets

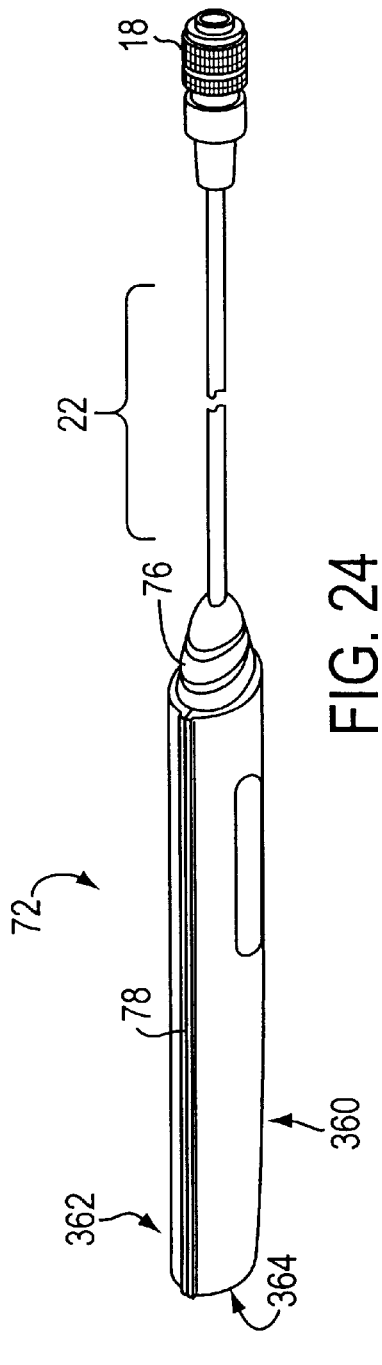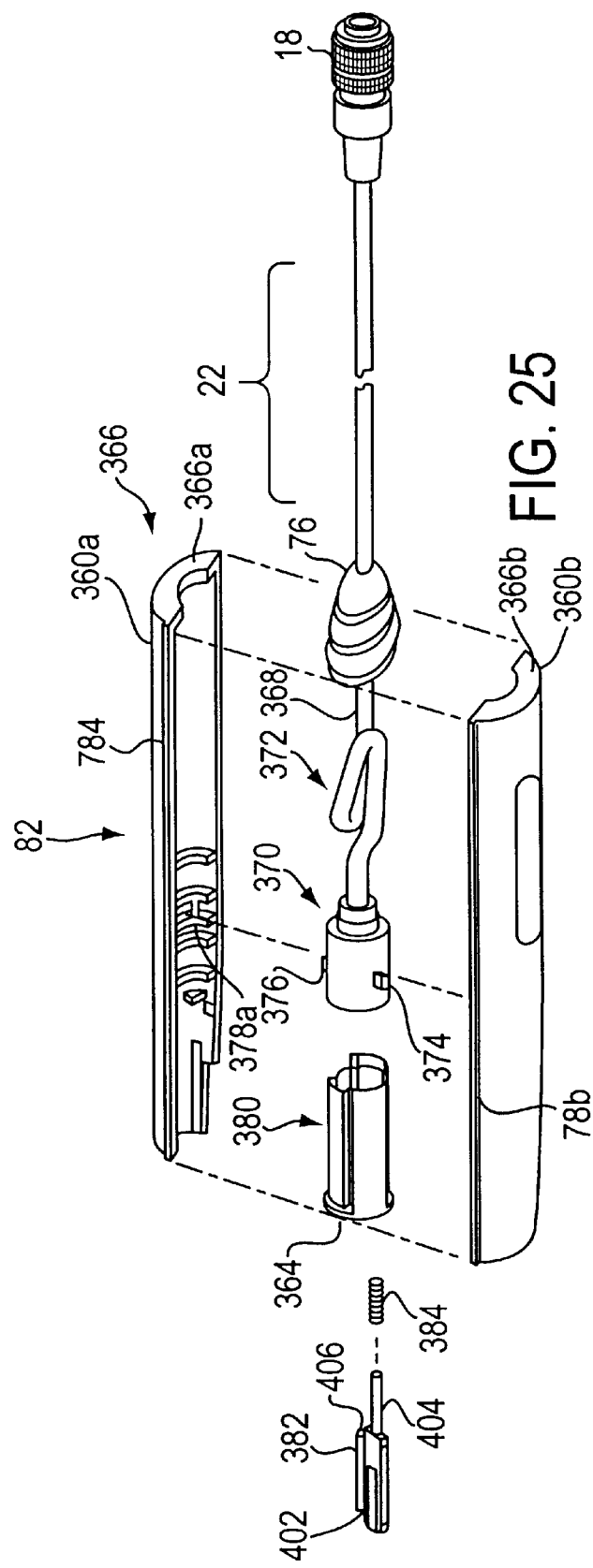

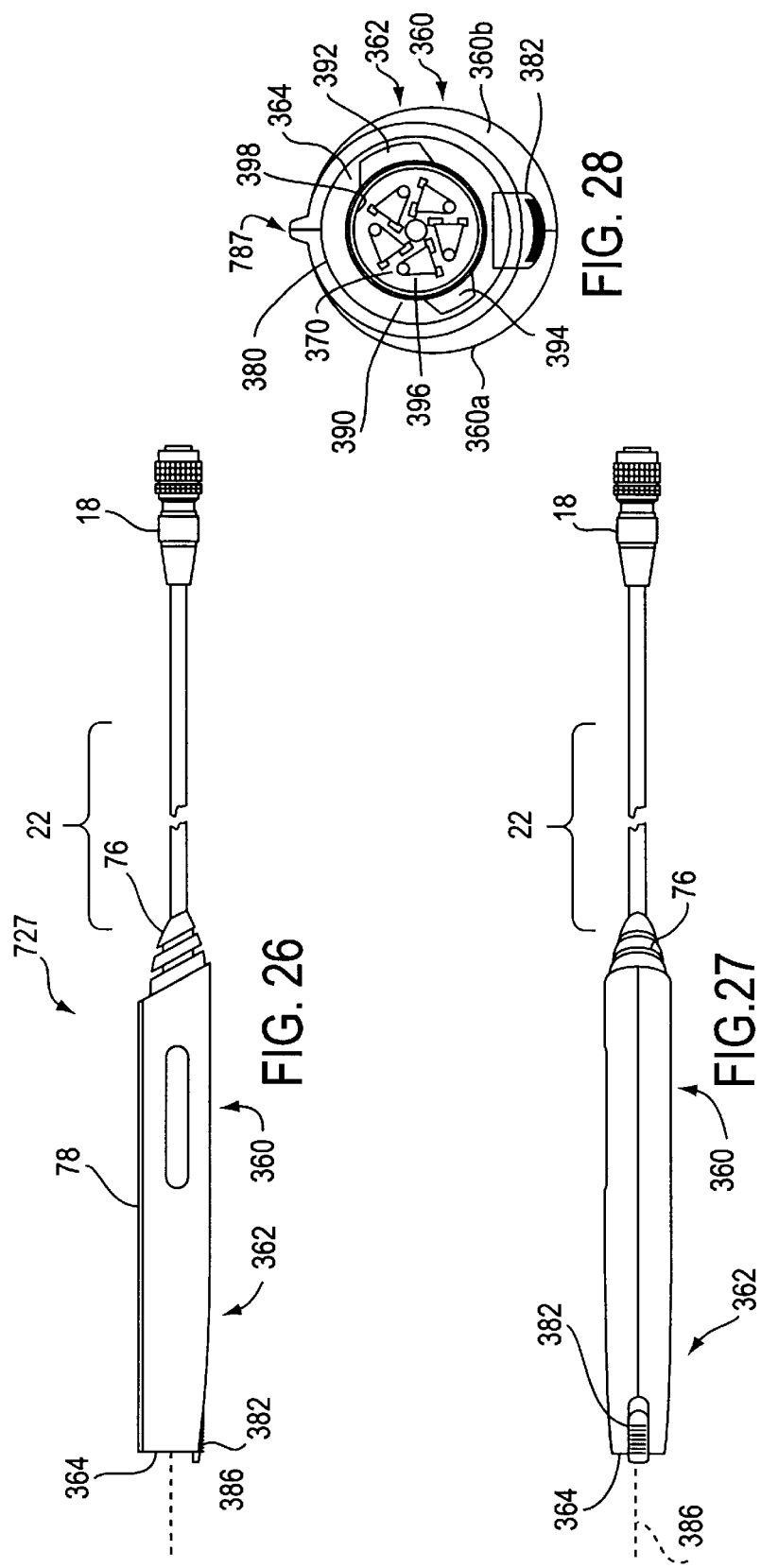

SURGICAL PROBE APPARATUS AND SYSTEM

BACKGROUND OF THE INVENTION

Current and historical procedures for the treatment of colon and rectal cancer have been based upon the natural history of tumor spread, and thence, upon operative and nonoperative options. Operative options generally have looked to the physical location and surgical resection of tumor. A variety of techniques have been brought to bear in the art with the purpose of aiding the surgeon in detecting and localizing neoplastic tissue as part of this surgical procedure. ("Neoplastic tissue", for present purposes, often is referred to as cancerous tissue, though malignant tumor and malignant tumor cells also are found in the terminology of the art. The term "neoplastic tissue" includes all of these.) A substantial amount of effort in aiding the surgeon in locating neoplastic tissue has been through the utilization of radiolabeled antibody for detection purposes. For example, one technique includes the scintillation scanning of patients injected with relatively high energy, e.g. $^{131}$I labeled antibodies. Such photoscanning or scintillation scanning provides scintigrams difficult to interpret or of little value for detection of small lesions because of blood pool background radioactivity. Computer subtraction of radioactive blood pool agents and the use of two labeled antibodies (one specific for the tumor and one non-specific) have been attempted to enhance imaging. Nevertheless, such techniques have been found to provide little, if any, useful information to the surgeon, especially over and above CAT scans, magnetic resonance imaging, and like traditional techniques.

Typically, large tumor is readily located by the surgeon by visualization at the operating theater as well as through palpation, i.e. the feel of a tumor as opposed to that of normal tissue. To achieve operative success, however, it is necessary for the surgeon to somehow locate neoplastic tissue at positions within the body cavity not accessible with vision, for example internally within the pelvic region or behind the liver or pancreas. It also is necessary for the surgeon to locate "occult" tumor at any position. Occult tumor or occult neoplastic tissue is that which is so diminutive in size as to be unidentifiable either by sight or feel. Failure to locate and remove such occult and non-visible tumors generally will result in the continued growth of cancer in the patient, a condition often misidentified as "recurrent" cancer. In general, conventional diagnostic techniques as, for example, use of the classic gamma camera and the like, fail to find or locate occult tumor. As tumor sites become smaller, the radionuclide concentrations at a given tumor site will tend to be lost, from an imaging standpoint, in the background radiation necessarily present.

U.S. Pat. No. 4,782,840 by Martin, M. D. and Thurston, Ph.D., entitled "Method for Locating, Differentiating, and Removing Neoplasms," issued Nov. 8, 1988 (the disclosure of which is expressly incorporated herein by reference) reviews such scintillation scanning technique and discloses a much improved method for locating, differentiating, and removing neoplasms. Such technique utilizes a radiolabeled antibody and a portable radiation detection probe which the surgeon may use intraoperatively in order to detect sites of radioactivity. Because of the proximity of the detection probe to the labeled antibody, the faint radiation emanating from neoplastic tissue at occult sites becomes detectable, for example, in part because of the inherent application of the approximate inverse square law of radiation propagation. The procedure is known as the Radioimmunoguided Surgery™ system (Radioimmunoguided Surgery being a trademark of Neoprobe Corporation, Columbus, Ohio) and is successful additionally because of a recognition that tumor detection should be delayed until the blood pool background of circulating radiolabeled antibody has had an opportunity to be cleared from the body. As a consequence, the photon emissions or radiation emitted by minor tumors compared to surrounding tissue becomes detectable in view of the proximity of the probe device to it. Fortuitously, the '840 patent discloses the ability of the radiolabeled antibody to remain bound to or associated with neoplastic tissue for extended periods of time with the radio tag still bound thereto. Moreover, even though the accretion of radioactivity at the tumor site decreases over time, the blood pool background and surrounding tissue (relative to the tumor sites) decrease at a much greater rate so that the radioactive sites can be determined readily utilizing a hand held probe positioned in close proximity with the tissue under investigation.

The instrumentation developed to support the radioimmunoguided surgery system has been called upon to meet rigorous performance criteria. Radiation emitted from occult tumor necessarily is very sparse and will emit to evoke a relatively low count rate upon detection. This low count rate, in turn, is developed with a corresponding count rate from the same radioisotope which is background radiation, albeit in itself low, but which must be accommodated for. The circuitry involved for such instrumentation is described, for example, in U.S. Pat. No. 4,801,803 by Denen, et al., entitled "Detector and Localizer for Low Energy Radiation Emissions", issued Jan. 31, 1989. To evaluate detected emissions and the counts generated therefrom with the instrumentation, a microprocessor-driven control program has been developed as is described in U.S. Pat. No. 4,889, 991, by Ramsey, et al., entitled "Gamma Radiation Detector with Enhanced Signal Treatment", issued Dec. 26, 1989.

This instrumentation supporting the probe device which is held by the surgeon and maneuvered within the body cavity is retained within a battery-powered console located within the operating room. Because of the low levels of signal evoked at the crystal detector within the probe, that device itself carries a preamplification stage for the purpose of generating a signal output suitable for transmission by cable or the like to the adjacent console. The preamplification stage performs in conjunction with a cadmium telluride crystal detector, and this combination of components is called upon to perform at the temperatures of the human body while undergoing calibration at substantially cooler temperatures found, for example, in the operating room environment This requirement has tended to reduce the energy level discrimination flexibility of the devices. U.S. Pat. No. 5,441,050 by Thurston, Ph.D. and Olson, Ph.D., entitled "Radiation Responsive Surgical Instrument," issued Aug. 15, 1995 describes an improved amplifier which achieves gain stability under temperature variations as well as an operation exhibiting low noise characteristics. The architecture of the hand-held probe, particularly as it is concerned with the mounting or supporting of the cadmium telluride crystal, has also been described, for example, in the noted U.S. Pat. No. 4,801,803; U.S. Pat. No. 4,893,013, by Denen, entitled "Detector and Localizer for Low Energy Radiation Emissions", issued Jan. 9, 1990; and U.S. Pat. No. 5,070,878, by Denen, entitled "Detector and Localizer for Low Energy Radiation Emissions", issued Dec. 10, 1991.

While improvements have been made which greatly increase the sensitivity of hand-held probes to sources of faint radiation, further improvements to these probes are called for. Bending the transmission cable excessively at either end might result in damage to the cable connectors as well as to the cable. To avoid these problems cables with more elaborate structuring can be procured, but such cables are more expensive and do not eliminate the problems caused by induced strain and deterioration over extended use.

Cleaning and sterilization of hand-held probes is also the subject of investigation. After each use, contaminants and bodily fluids must be removed from the probe, transmission cable, and the connector between the probe and the cable. To be able to remove all of the exterior particles and fluid, the probe surfaces must be smooth and free of cracks and recesses. Such a requirement necessarily increases the cost of manufacture. In addition, the connector, into which the transmission cable is inserted, consisted of a complex opening with a depth of up to three-eighths of an inch which has proved difficult to clean.

Sterilization of instruments and equipment is essential in a surgical setting to kill pyogenic organisms, such as staphylococcus aureus, which are not killed by alcohol or other cleaning agents. There are currently a number of methods available for the sterilization of surgical instruments. One of the oldest and quickest ways of sterilizing surgical instruments is by the process of autoclaving. The instrument is placed under high pressure and the temperature is raised to around 140 degrees Celsius. Such a process could not be used for previous probe models because of the thermonic effect on the delicate internal circuitry of the probe. As a result, most probes are sterilized with ethylene oxide gas, EtO. This process is more time-consuming than autoclaving often requiring twenty-four hours for completion. In addition, care must be taken in handling the gas because it is flammable, toxic, and corrosive to certain types of plastic.

BRIEF SUMMARY OF THE INVENTION

The present invention is addressed to a surgical system and apparatus wherein a hand-held probe is employed in locating sources of radiation emitting from tissues of the body. Practical cleaning and sterilization of the probe instrument of the surgical system is achieved through the utilization of a dual component design. With this design, a permanent, reusable forward or front end detector component is provided which incorporates more costly and delicate elements such as a crystal detector, radiation transmitting window, detector mount, and preamplification circuitry. These features are mounted within a detector housing having regular, smooth and thus cleanable surfaces formed of materials which are immune from damage otherwise occasioned by heat sterilization procedures. Being readily cleanable and heat sterilizable, this detector component is usable repeatedly and possibly with the desirably more rapid turn-around intervals made possible with heat sterilization procedures.

The permanent, reusable front-end detector component is employed in conjunction with a disposable handle component fabricated with less expensive materials and under a design involving a minimum of components. Accordingly, the handle component may be discarded after its use, the need to clean it and sterilize it after such use being eliminated. In this regard, the handle component design includes an elongate electrical cable which is permanently connected with an electrical contact assembly supporting a pattern of electrical contacts. When the sterilizable detector component is attached to the handle component, these terminals engage the corresponding electrical contact surfaces of an electrical terminal assemblage mounted upon the detector. A latching arrangement provides for a releasable connection of the permanent and disposable components of the system as well as assuring a proper electrical contact surface to electrical contact alignment and releasable coupling. An elastomeric seal within the handle assures the integrity of this multi-lead temporary electrical connection.

Releasable interconnection of the detector and handle is achieved by utilization of a smooth, cylindrical positioning shaft which extends from the detector housing in conjunction with a receiving cavity which is provided within a retainer portion of the handle. The outwardly disposed tip surface of this positioning shaft carries a pattern of smooth electrical contact surfaces which confront and then make proper electrical contact with the corresponding pattern of handle-mounted terminals.

Other objects of the invention will, in part, be obvious and will, in part, appear hereinafter.

The invention, accordingly, comprises the system and apparatus possessing the construction, combination of elements, and arrangement of parts which are exemplified in the following detailed description.

For a fuller understanding of the nature and objects of the invention, reference should be had to the following detailed description taken in connection with the accompanying drawings.

BRIEF DESCRIPTION OF THE DRAWINGS

FIG. 24 is a pictorial view of the handle component of the invention;

FIG. 25 is an exploded view of the handle component shown in FIG. 24;

FIG. 26 is a side view of the handle component of the invention;

FIG. 27 is a bottom view of the handle component of the invention;

FIG. 28 is a left side view of the handle component of FIG. 27;

DETAILED DESCRIPTION OF THE INVENTION

Figure 1:
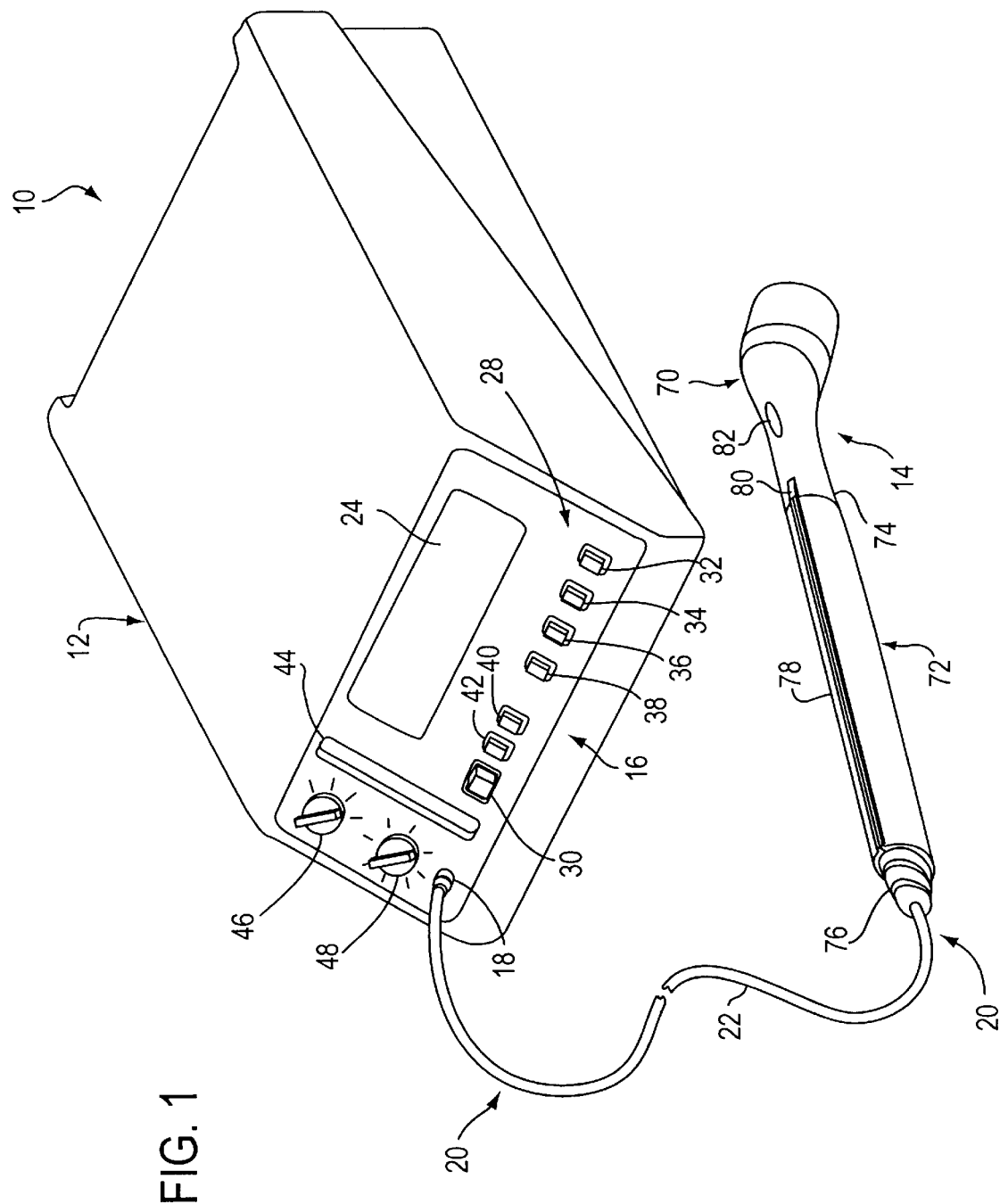
FIG. 1 is a pictorial representation of the system and instrumentation of the invention.

Referring to FIG. 1, a radioimmunoguided surgical system (RIGS™) incorporating the features of the invention is represented generally at 10. System 10 includes a signal treatment and control assembly or console represented generally at 12 to which is coupled a probe or probe instrument represented generally at 14. The control console 12 is configured for both carrying out radioimmunoguided surgery and for tracking radiopharmaceuticals injected at the situs of a tumor to locate a lymph sentinel node. In the latter regard, the photon count evaluation, including lower threshold and upper limit windowing and discriminator functions of the RIGS system are commonly utilized. That RIGS system is described, for example, in U.S. Pat. No. 4,801,803, entitled "Detector and Localizer for Low Energy Radiation Emissions" by Denen, Thurston, and Ramsey, issued Jan. 31, 1989, and assigned in common herewith. The forward face 16 of console 12 includes a coupling or connector 18 which provides for electrical signal communication and power supply association with the probe instrument 14 via a transmission assembly represented generally at 20, which includes a flexible cable 22. Forward face 16 of console 12 additionally carries a relatively large liquid crystal display (LCD) readout 24 as well as an array of push-type switches 28. This array of switches permits the microprocessor-driven control assembly 12 to carry out an instructive or "user friendly" dialogue with the practitioner. In addition to a conventional on and off rocker switch 30, the switches provided at forward face 16 include such function selection switches as a count mode switch 32, a reset count switch 34, a background count or squelch switch 36, a sound control switch 38, and up and down incrementing switches shown, respectively, at 40 and 42.

Also mounted at the forward face 16 of console 12 are components, for example, employed with the lymph tracking features of the system 10. In this regard, a linear segmented LED array 44 is included for the purpose of providing a visual cuing aspect as to peak count rate level. A range selection switch is provided at 46. Switch 46 permits the practitioner to select any of four count rate ranges to achieve full scale readouts when the system 10 is employed in tracking radiopharmaceuticals. These ranges may, for example, be 0–1000 counts per second; 0–2500 counts per second; 0–10,000 counts per second; and 0–30,000 counts per second. Below the knob actuated range switch 46 is a knob actuated threshold switch 48 which is used to provide a count rate threshold input. The threshold is a percentage valuation of any one of the count ranges established at switch 46. This thresholding is a variation of the background count or squelch procedure carried out in connection with switches 34 and 36. In this regard, the function of reset count switch 34 is to derive a count value over a preset interval, for example, 2 seconds. The background count switch 36 is employed in conjunction with reset count switch 34 to develop a statistical count value based upon a measured background count rate. For example, in the RIGS procedure, the probe instrument 14 initially is positioned in the vicinity of the heart or aorta in order to obtain a blood pool background count rate. The interval during which this rate is determined is, for example, 5 seconds. A microprocessor-based control system of console 12 then calculates a statistically significant value, for example a predetermined number of standard deviations of the basic background count rate to derive a statistically significant threshold count rate level. This, for example, may be 3 sigma above a base count rate. The ranging procedure is referred to by surgeons as "squelching". Operating in conjunction with that threshold level in the RIGS procedure, the system 10 provides the surgeon with audible cues indicting that a high probability of tumor involvement is present at a location closely adjacent the position of the forward window of probe instrument 14. This squelching procedure also may be utilized in conjunction with the detecting and locating of sentinel lymph nodes in connection with breast cancer or melanoma studies or procedures. However, with the system 10, an adjunct system is provided for that purpose.

Figure 2:
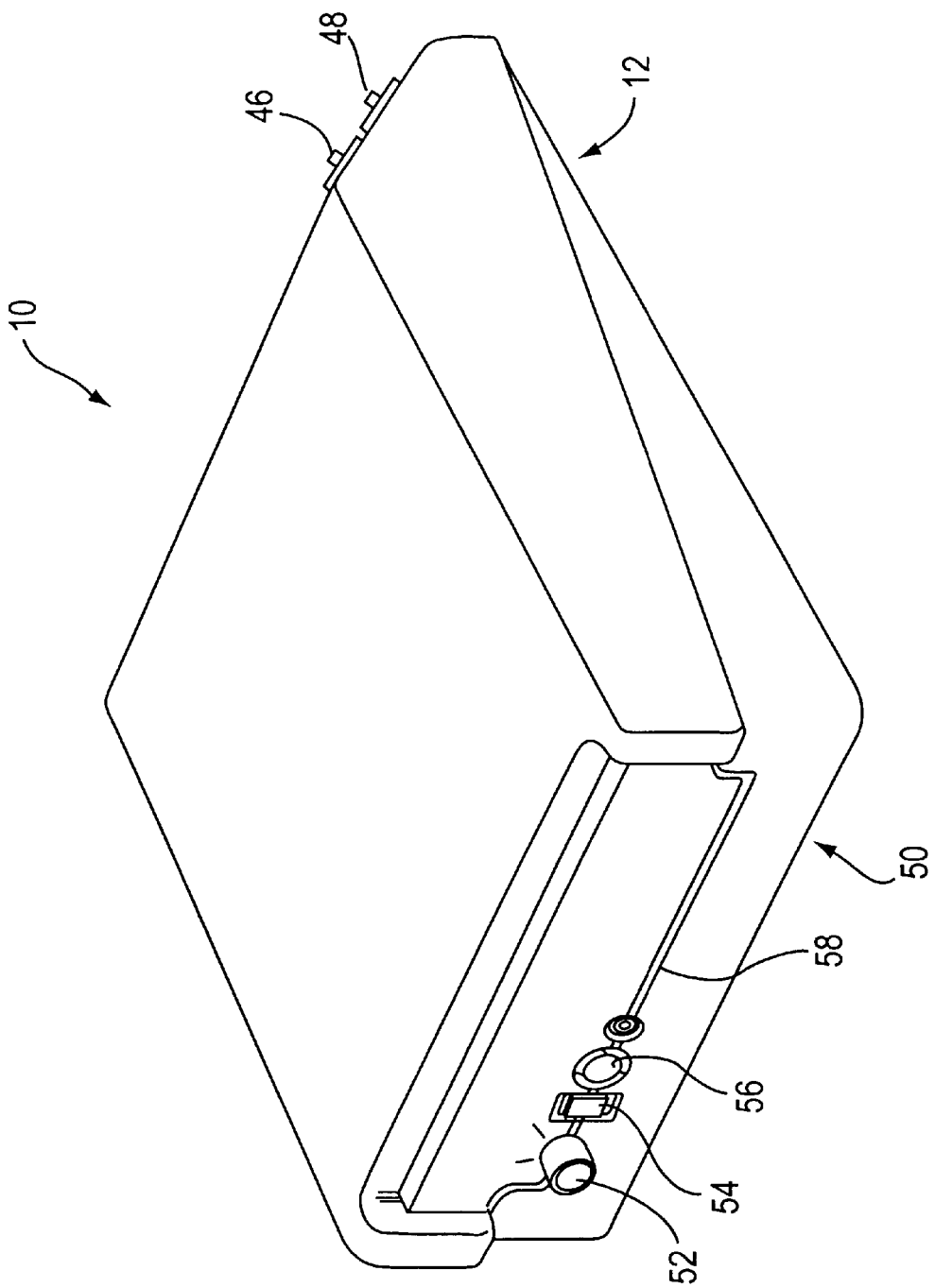
FIG. 2 is a pictorial representation of the rear portion of the console illustrated in FIG. 1.

Referring to FIG. 2, a view of console 12 again is provided, however, revealing the structuring of the rear wall 50 thereof. At this wall 50, there is located a mode selection switch 52 which is manually actuated to either of two positions, one electing that the system 10 operate in its standard RIGS mode, and the other electing that system 10 operate in conjunction with the adjunct system for carrying out sentinel node detection procedures and the like. Adjacent switch 52 is a pushbutton-type calibration switch 54 which provides for carrying out a calibration of the system. Also mounted at the wall 50 are a fuse access assembly 56 and a battery charger input connector 58.

Figure 3A:
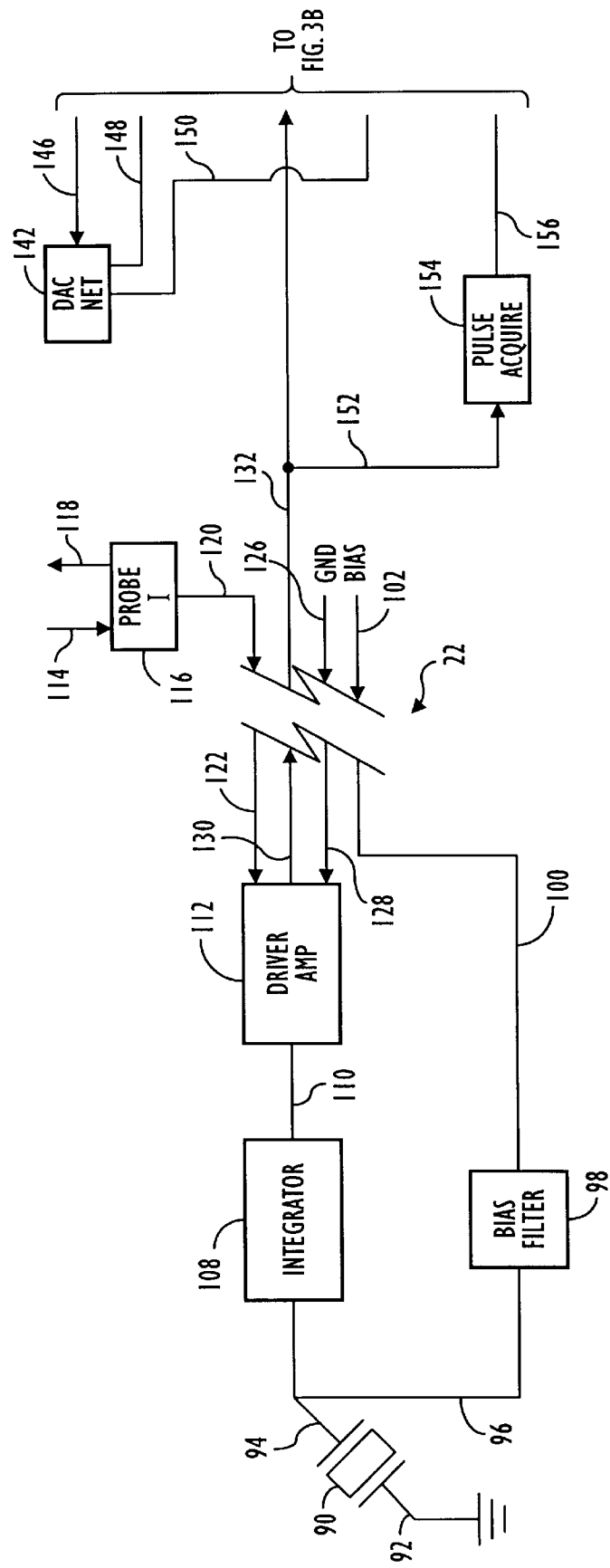
FIGS. 3A and 3B combine as labeled thereon to provide a block diagrammatic representation of the circuits employed with the control assembly and probe shown in FIG. 1.

Returning to FIG. 1, the probe 14 is seen to be formed of two complementary components, a forward detector component 70 within which are mounted a radiation responsive crystal, for example a cadmium-zinc-telluride crystal, along with a preliminary treatment circuit, for example, a preamplifier integrator stage as well as associated amplification stages. The detector component 70 is configured of a polymeric material which is heat sterilizable and is configured with very smooth surfaces to enhance its cleanability. These more expensive components then are permanent in nature in that the detector 70 is reusable over an extended period of time. Detector component 70 is removably inserted within a disposable handle component 72. These two components 70 and 72, when releasably connected together, will reveal mutually abutting contact and camming surfaces which join as represented at 74. The disposable handle component 72 is permanently attached to the flexible cable 22 and a cable relief component is shown at 76. Along the top of the handle component 72 is an orientation ridge 78. When the detector component 70 is in its appropriate operational orientation with respect to handle component 72, a small ridge extension 80 will align with ridge 78. The ridges 78 and 80 give the surgeon a tactile cue as to the instantaneous orientation of probe 14. To further aid in providing a tactile cue as to the orientation of the detector component 70, a flat finger rest 82 is formed in the top of that component in alignment with ridges 78 and 80 and generally perpendicular with respect to them Referring to FIGS. 3A and 3B, a block diagrammatic representation of the circuitry employed with the system 10 is portrayed. These figures should be considered in mutual adjacency in the manner labeled thereon. In FIG. 3A, a radiation detector such as a cadmium zinc telluride crystal suited for mounting within the detector component 70 is represented at 90. Crystal 90 is shown having one face coupled to ground through line 92, while the opposite, electrically biased face thereof coupled via lines 94 and 96 to a bias filter represented at block 98. The input to filter 98 is represented at line 100 as being applied through the cable as described earlier at 22, which number reappears in the instant figure. The biased input is seen, as represented at line 102, emanating from a multi-output power supply shown in FIG. 3B at block 104. These various outputs from the power supply 104 are represented, in general, by an arrow 106.

Figure 3B:
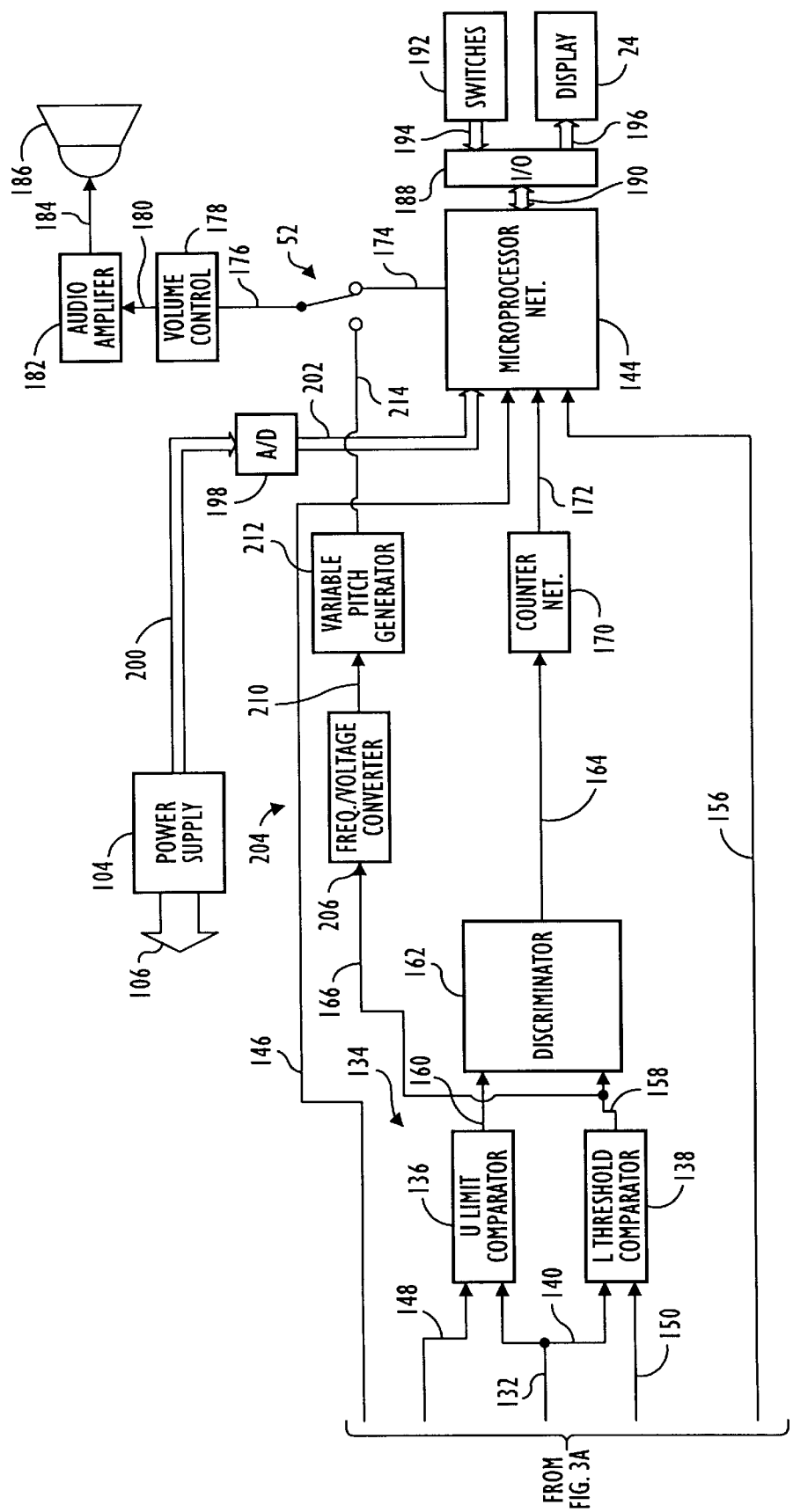

Returning to FIG. 3A, line 94 from the crystal 90, carrying detector outputs corresponding with radiation emissions impinging upon the crystal, is seen to extend to an integrator stage represented at block 108. This integrator stage 108 forms part of the preamplification function contained within the forward detector component 70. The integrated valuation of detected radiation emissions then is shown directed, as represented by line 110, to a driver amplification network shown at block 112. A preferred preamplification circuit comprised of blocks 108 and 112 is marketed as a charge sensitive preamplifier, part No. eV-5167 by eV Products Division of II–VI Incorporated of Saxonburg, Pa. 16056. The amplification stages represented at block 112 also will be seen to be incorporated within the forward heat sterilizable detector component 70. A d.c. power supply is provided from the power supply represented at block 104 and arrow 106 for the preamplification function (FIG. 3B). This power supply is directed, as represented at line 114, to a probe current network represented at block 116. Under microprocessor control as represented at line 118, the network 116 develops signals, for example, determining whether the cable 22 has been properly connected to console 12. Delivery of the d.c. power supply for the preamplification stages is represented at lines 120 and 122. Line 122 forms a component of flexible cable 22. Instrument ground which is generated from the power supply at block 104 and as represented at arrow 106 (FIG. 3B) is shown at lines 126 and 128, the latter line being part of cable 22.

The preamplification stage is a signal treatment circuit which provides count outputs which are presented along line 130 of cable 22 for introduction to the control assembly 12, the corresponding signal carrying line of which is shown as line 132. Line 132 extends to the input of an energy window network represented in FIG. 3B in general at 134, which functions to evaluate the count outputs to derive validated photon count signals. Looking to FIG. 3B, it may be observed that the energy window network 134 includes an upper limit comparator represented at block 136, as well as a lower threshold comparator represented at block 138. The count output or photon event signals at line 132 are submitted simultaneously to each of these comparator functions 136 and 138, as represented at line 140. Correspondingly, the comparison values or limits associated with the upper limit comparator 136 are applied from a digital-to-analog converter (DAC) 142 seen in FIG. 3A at block 142. Converter 142 is under the control of a microprocessor network represented at block 144, such digital control to device 142 being asserted as represented at line 146. Thus, the upper limit value asserted at the comparator 136 is provided at line 148 from DAC 218. Correspondingly, the lower threshold value for comparator function 138 is asserted from DAC 142 via line 150. FIG. 3A also reveals that the signals at line 132 are directed, as represented at line 152 to a pulse acquire function represented at block 154. Network 154 functions, when activated by the microprocessor function 144, to acquire the value of the highest amplitude of the pulse witnessed at line 132. Periodically, this information then is transmitted to the microprocessor function 144 as represented by line 156. Representing a form of peak detector, the network 154 sometimes is referred to as a "snapshot circuit".

With the arrangement shown, the probe 14 assemblage derives count outputs in response to photon emissions which are confronted at the forward face of crystal 90. Those count outputs will have an amplitude corresponding to the energy of interest of the photon emissions. Additionally, the signals may represent spurious phenomena such as cosmic rays and the like. Accordingly, the energies of the count outputs or amplitudes thereof are evaluated at the energy window network 134 as seen in FIG. 3B. The lower threshold comparator 138 will promulgate a pulse at line 158 when the signal asserted thereat exhibits an amplitude of value equal to or above a threshold value established, as noted above, from line 150. Correspondingly, the count output signals from line 140 will be evaluated by the upper limit comparator function 136 such that when the count output signal exhibits an amplitude of value above the upper limit value established from line 148, a pulse will be promulgated at line 160. These outputs from lines 158 and 160 then are directed, for the RIGS mode of operation, to the input of an asynchronous sequential fundamental mode discriminator circuit represented at block 162. Circuits as at block 162, while being sequential in nature, are not synchronized in any way with a clock signal. Such circuits as at block 162 are described in U.S. Pat. No. 5,475,219 by Olson, entitled "Validation of Photon Emission-Based Signals Using an Energy Window Network in Conjunction with a Fundamental Mode Discriminator Circuit", issued Dec. 12, 1995, and assigned in common herewith. The discriminator function represented at block 162 serves to generate photon event outputs for count associated signals in the form of pulses at line 164. Such pulses occur with the presence of a count output signal at line 132 which represents a photon emission which is valid from the standpoint of the energy range of interest associated with it.

For the RIGS component of the system 10, the output at line 164 is provided at line 164 to a counter network represented at block 170. These pulses are counted by the network 170, whereupon, as represented at line 172, count data is submitted to the microprocessor network 144 for statistical analysis. The function of counter network 170 may be implemented in software as described in the above-referenced U.S. Pat. No. 4,889,991. Microprocessor network 144 performs under a variety of operational modes depending upon the user inputs to the function switches at array 28 (FIG. 1) and calibration switch 54 (FIG. 2). In general, it functions to provide outputs for two output components, one aural type generated from a speaker, and the other a visual output at display 24. Generally, a "siren" type of signal manifested with a predetermined frequency variation is asserted as represented by line 174 through mode switch 52 and line 176 to a volume control function represented at block 178. Control over the volume control function 178 remains notwithstanding any changing of switch 52 to the adjunct mode of operation. The output from control 178 at line 180 is directed to an audio amplification circuit represented at block 182. This circuit at block 182, in turn, as represented at line 184, drives a speaker 186. With the noted siren arrangement, the frequency output from speaker 186 increases with an exponential change from 20 Hz to 1200 Hz when the average count rate determined by system 10 exceeds a preset threshold level which is statistically significant over background count rates. The siren mode is accessed by the user from console 12 by sequentially actuating switch 36, then switch 34. This siren mode of performance is described in detail in the above-referenced U.S. Pat. No. 4,889,991 by Ramsey and Thurston.

Microprocessor network 144 performs in conventional fashion with an input/output network as represented at block 188 and dual directional arrow 190. This input/output port function 188 provides for appropriate scanning of pertinent console 12 mounted switches as represented at block 192 and arrow 194. The output port also drives the display 24 as identified by the same numeration in block form, as represented by arrow 196. Further, the microprocessor network 144 may be employed to monitor the performance of the power supply represented at block 104. This is shown being carried out by the interaction of microprocessor network 144 with an analog-to-digital converter shown as block 198 and having an association represented by arrows 200 and 202. The converter 198 functions to digitize analog values at the power supply 104 for submittal to microprocessor network 144 for diagnostic purposes.

Components of the adjunct system of system 10 are represented in general at 204 in FIG. 3B. The components of system 204 include a frequency-to-voltage converter represented at block 206 which responds to the count associated signals from the lower threshold comparator at block 166 as represented at line 158 and 166 to provide at line 210 a rate output level signal corresponding with the frequency of those count associated signals. This signal will be provided as a d.c. voltage level which extends within a dynamic range of, for example, 0–2.5 volts. That signal then is directed to a variable pitch generator function represented at block 212. The function at block 212 serves to provide an initial ranging feature associated with switch knob 46, and a count rate thresholding feature which may be controlled from knob 48. Additionally included in the function 212 is a post thresholding amplification network having a gain corresponding with the threshold level value established by the practitioner to permit full scale performance of the speaker 186 and linear LED array 44 (FIG. 1). The output of function 212 is shown at line 214 extending to one terminal of switch 52.

Figure 4:
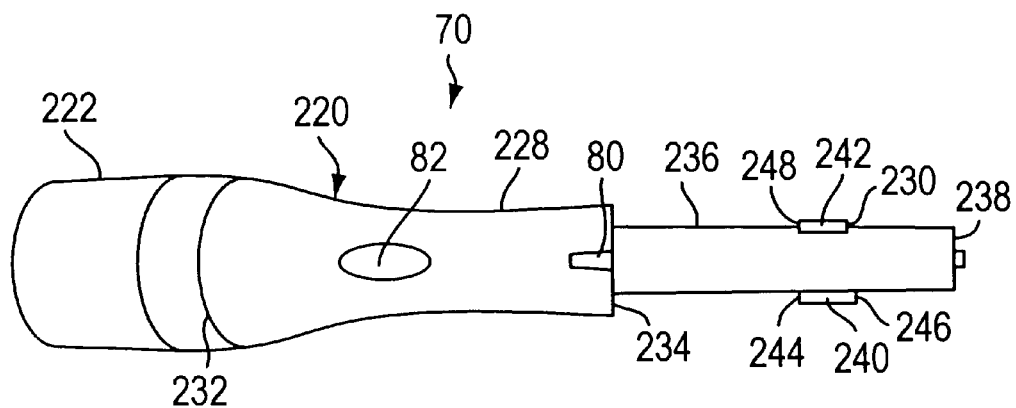
FIG. 4 is a top view of a detector component employed with the invention.
Figure 5:
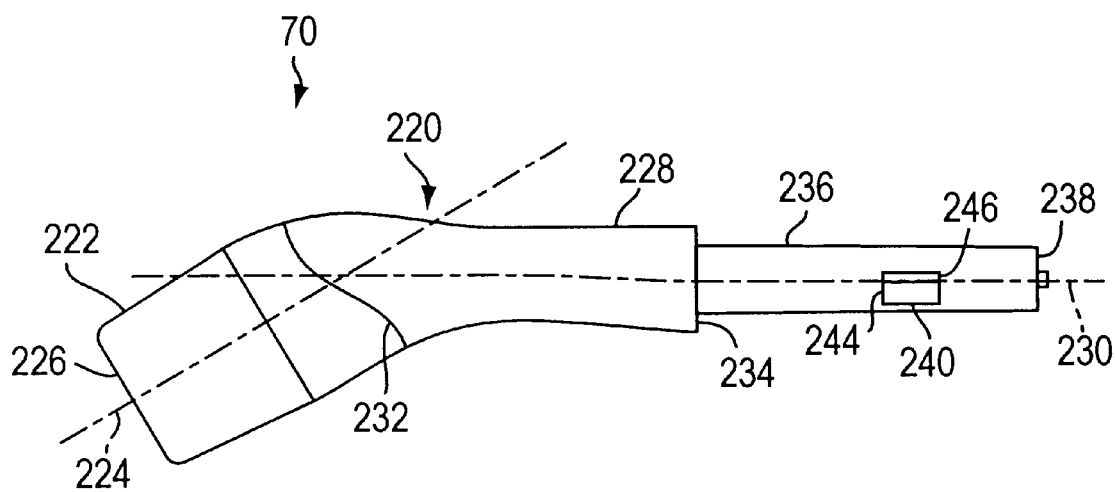
FIG. 5 is a side view of the detector component of FIG. 4.
Figure 36:
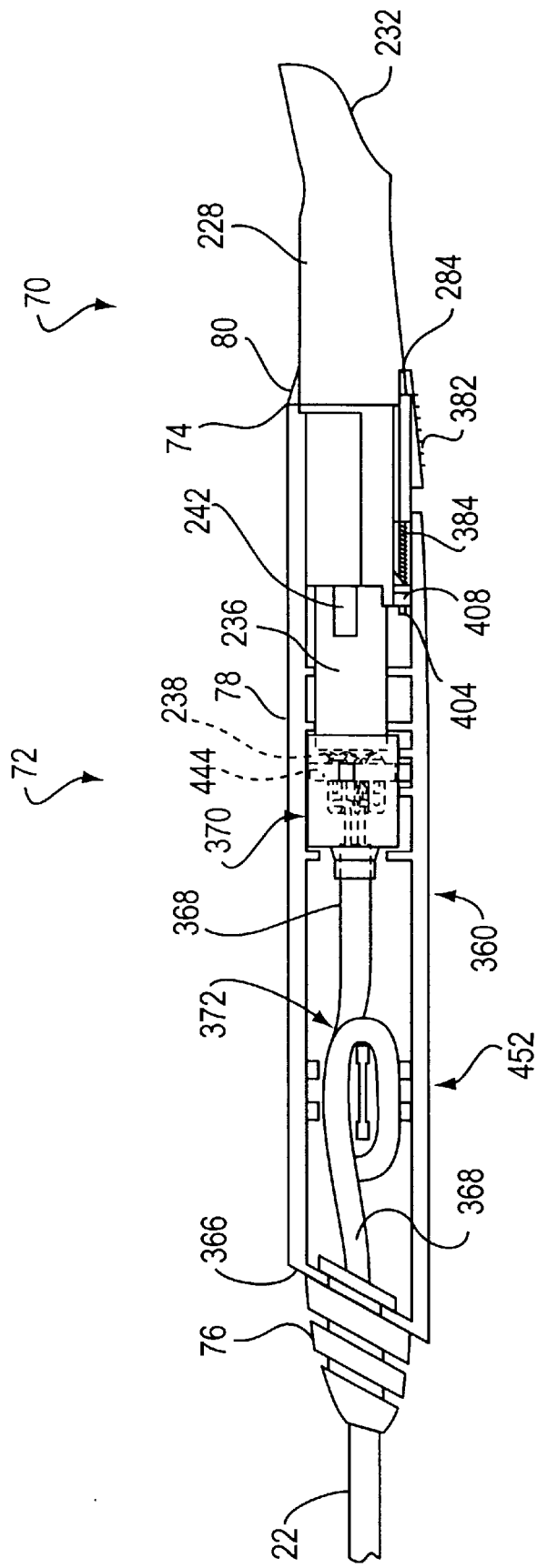
FIG. 36 is a partial sectional view of a united detector and handle component assemblage of the invention.

Now looking in detail to the structuring of the forward detector component 70, reference initially is made to FIGS. 4 and 5. The top view represented in FIG. 4 reveals that the component 70 is formed having a detector housing 220 which includes a forward portion 222 which is seen in FIG. 5 to extend along a detector axis 224 to a forward surface 226. A support portion 228 extends rearwardly from the forward portion 222 along a support axis seen in FIG. 5 at 230. That figure also reveals an S-shaped union or joint 232 at which portions 222 and 228 are connected with an adhesive. The enhanced amount of surface for achieving an adhesively assembled joint improves the reliability of such a union. FIG. 4 reveals the earlier-noted finger rest 82 and ridge component 80. Portion 228 extends along the axis 230 to a contact positioning surface 234 from which extends an integrally formed cylindrical positioning shaft 236. Shaft 236 extends a predetermined distance from surface 234 to an electrical contact support surface 238. Formed integrally with the positioning shaft 236 are two orientation bosses as seen at 240 and 242. The principal orientation boss is that at 240 which is seen to be configured having an upper cam follower surface 244 and an oppositely disposed lower cam follower surface 246. Correspondingly, orientation boss 242 is configured having an upper cam follower surface 248 which is coplanar with surface 244. However, the lower cam follower surface 250 of orientation boss 242 is within a plane located forwardly along the support axis 230 as compared to the location of cam follower surface 246 of orientation boss 240. This configuration is provided for purposes of facilitating manual insertion of positioning shaft 236 into a receiving cavity within the handle component 72 (FIG. 36). The widthwise circumferential extent of orientation boss 240 also is greater than the corresponding widthwise extent of orientation boss 242.

Figure 6:
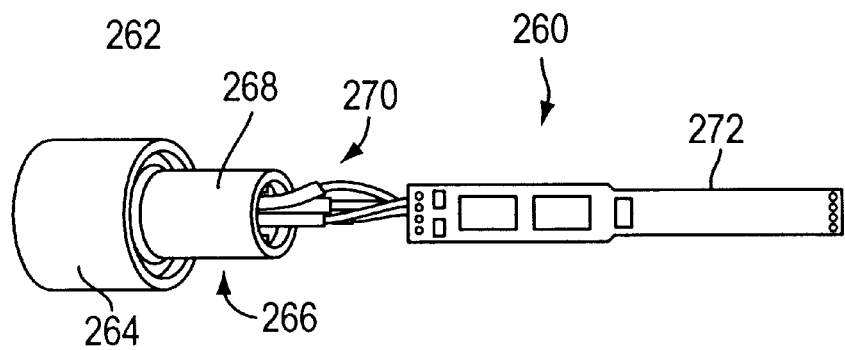
FIG. 6 is a pictorial view of an instrumentation subassembly employed with the detector component of FIG. 4.

Referring to FIG. 6, an instrumentation sub-assembly which is mounted within the detector component 70 is revealed generally at 260. The sub-assembly includes a forwardly disposed crystal containing assemblage shown generally at 262. The outwardly disposed component of this assemblage 262 is a cup-shaped fomaceous cushion 264. Extending rearwardly from assemblage 262 is a shielded tube-like circuit retainer assembly which also is covered by a tube-shaped fomaceous cushion 268. Leads represented generally at 270 are seen extending from the circuit retainer assemblage 266 for connection with a thin elongate circuit board 272. The circuit board 272, in general, will support surface mounted components corresponding with the amplification function described at block 112 in connection with FIG. 3A.

Figure 7:
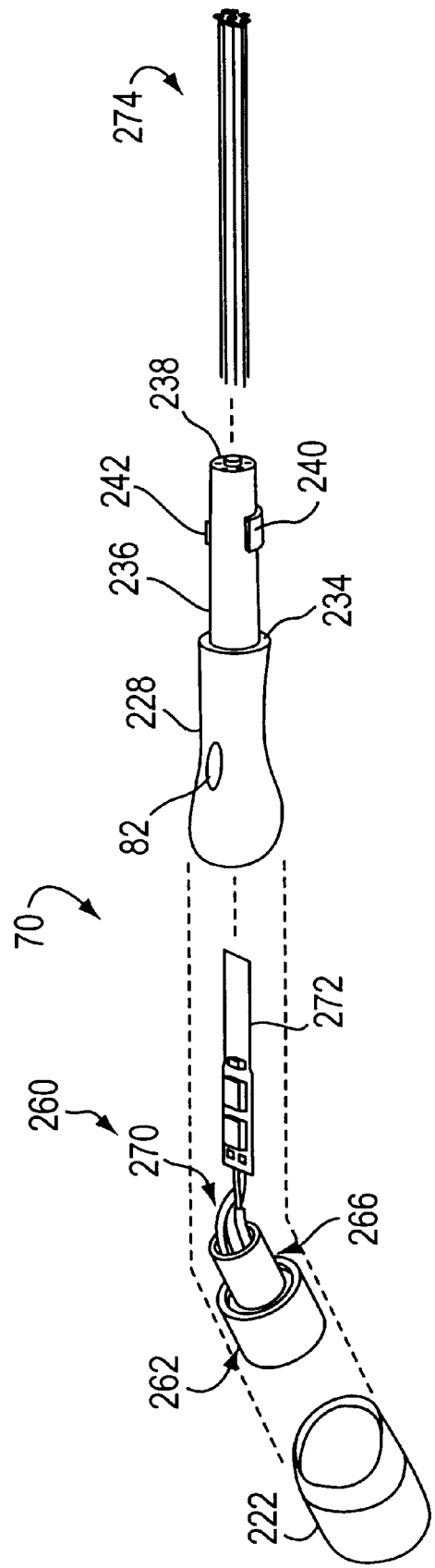
FIG. 7 is an exploded view of the detector component of FIG. 4.

Looking to FIG. 7, an exploded view of the association of the instrumentation sub-assembly 260 with the forward portion 222 of the detector housing as well as the rearward portion 228 thereof is provided. In this regard, the crystal containing assembly 262 fits within the internal cavity of forward portion 222, while circuit retainer assemblage 266, the leads 270, and circuit board 272 are mounted within a corresponding cavity within rearward portion 228. Additionally seen in FIG. 7 is an electrical terminal assemblage represented generally at 274 which supports contact surfaces and corresponding leads which are mounted at the electrical contact support surface 238 and extends within the positioning stem 236 to a union with the circuitry of the sub-assembly 260.

In general, the detector component housing is configured with smooth and regular surfaces for the purposes of enhancing its cleanability. To provide for heat sterilization, the housing may be formed, for example, of a polyphenyl-sulfone material.

Figure 8:
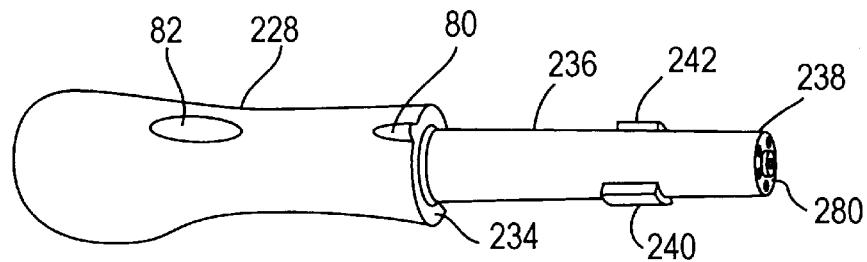
FIG. 8 is a pictorial view of the support portion of the detector of FIG. 4.
Figure 9:
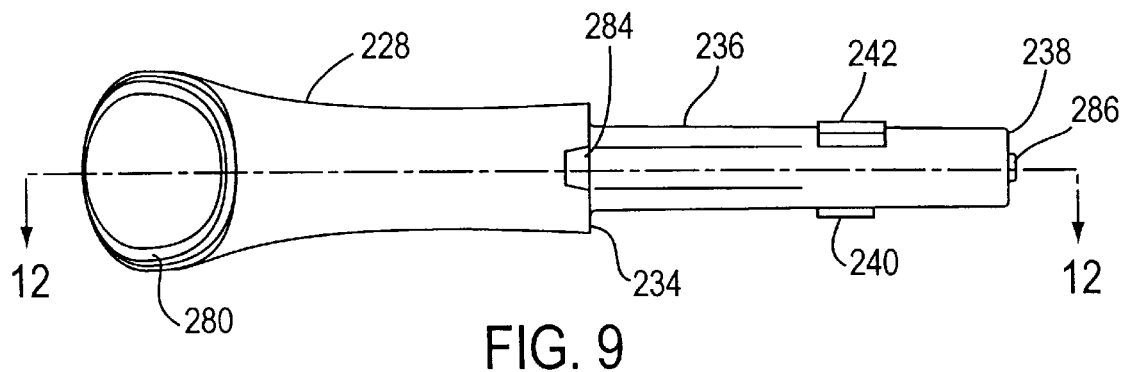
FIG. 9 is a bottom view of the support portion of the detector shown in FIG. 8.
Figure 10:
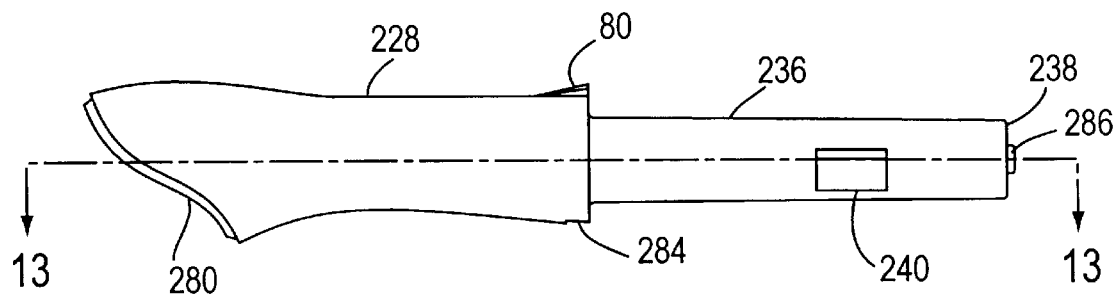
FIG. 10 is a side view of the support portion of the detector shown in FIG. 8.

Referring to FIG. 8, a pictorial view of the rearward portion 228 of the detector component housing is revealed. In the figure, electrical contact support surface 238 at the end of positioning shaft 236 is seen to support a pattern of five discrete electrical contact surfaces represented generally at 280. FIG. 9 reveals a bottom view of rearward portion 228, showing the forwardly disposed edge 282 which, as seen in FIG. 10, is configured with an S-shaped profile for enhancing its adhesive union with forward housing portion 222 (FIG. 7). FIG. 9 also reveals that a latching notch 284 is formed within the support portion 228 and extends forwardly from the contact surface 234. This notch will be seen to cooperate with a spring bias latching component, the combination functioning to aid in the proper rotational orientation of shaft 236 and its associated discrete contact surfaces 280. FIG. 9 also reveals that the orientation bosses 240 and 242 are only substantially diametrically opposite from each other. This is for purposes of developing mechanical stop functions also associated with the appropriate and facile insertion orientation of the supporting stem 236 within the handle component 272 (FIG. 1).

Figure 11:
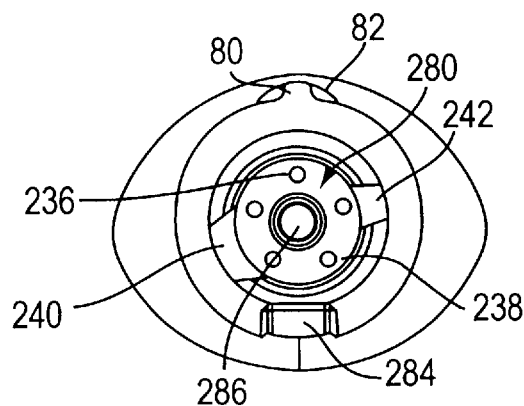
FIG. 11 is an end view of the detector component of FIG. 4.
Figure 12:
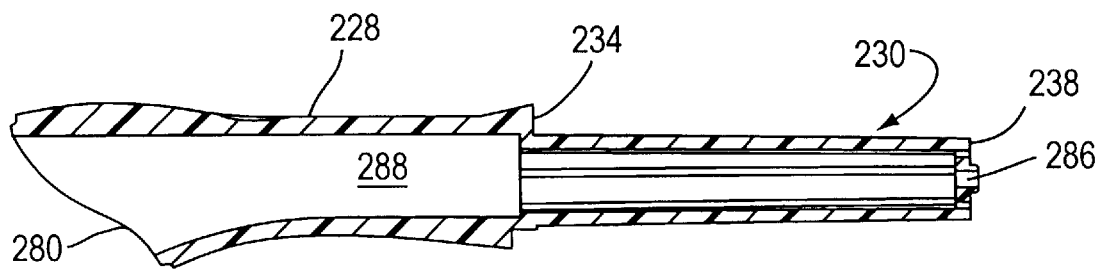
FIG. 12 is a sectional view taken through the plane 12—12 shown in FIG. 9.
Figure 13:
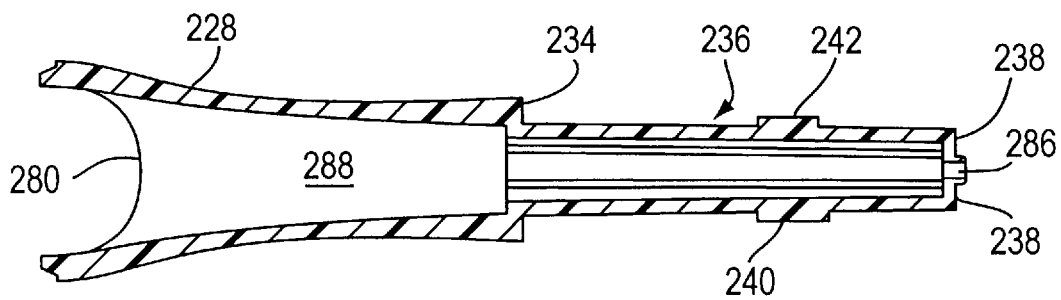
FIG. 13 is a sectional view taken through the plane 13—13 shown in FIG. 10.

Referring to FIG. 11, a rear view of rearward portion 228 is revealed. In this view, the noted orientations of orientation bosses 240 and 242 are revealed. Additionally, the larger circumferential widthwise extent of orientation boss 240 with respect to that of orientation boss 242 becomes apparent. Further, the five discrete electrical contact surfaces 280 are seen to be spaced radially at 72° intervals. The figure also reveals a filler port 286 which is utilized for filling the internal cavities of the rearward portion 228 with a polymer to stabilize the contents thereof. In the latter regard, reference is made to FIGS. 12 and 13 wherein the inner cavity developed within the rearward portion 228 is revealed at 288.

Figure 14:
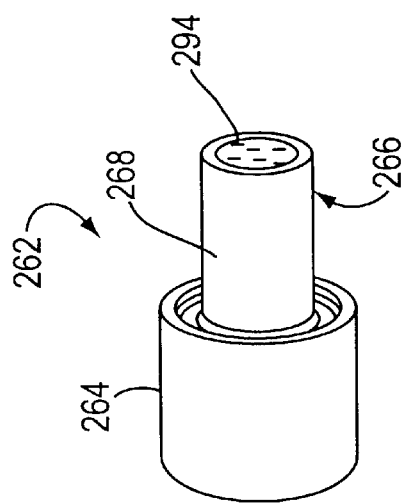
FIG. 14 is a pictorial view of the detector crystal and preamplification component shown in FIG. 7.
Figure 15:
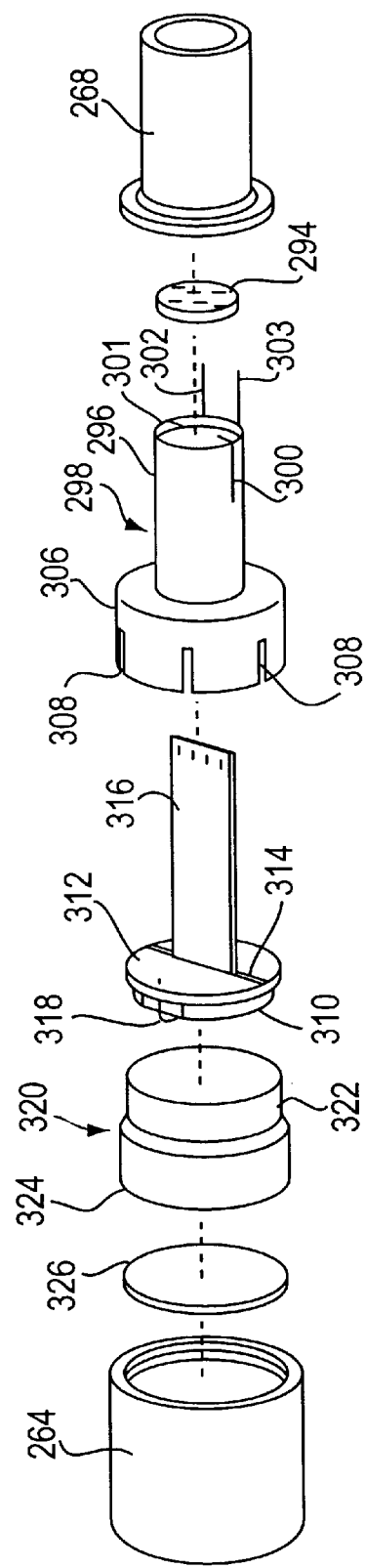
FIG. 15 is an exploded view of the assembly shown in FIG. 14.

Looking to FIGS. 14 and 15, the crystal containing assembly 262 is revealed. In FIG. 14, the circuit retaining assembly 266 is seen to be rearwardly enclosed by a shield end cap 294 having openings formed therein through which the lead 270 as described in connection with FIG. 6 may extend. Turning to FIG. 15, the cylindrical-shaped foamaceous cushioning component 268 reappears along with the shield end cap 294. That end cap 294 fits within the end of a tubular extension 296 of an electromagnetic shield housing represented generally at 298. Cap 294 further is coupled with two of four instrument ground wires 300 and 301 which are mechanically and electrically coupled to the extension 296, a remaining two such wires as at 302 and 303 being seen protruding outwardly. The shield 298 is formed, for example, of brass and is configured having a diametrically expanded forward portion 306 which is formed with slots, certain of which are identified at 308 to facilitate its interconnection with a forward component. Next in the sequence is a detector crystal 310 formed, for example, of cadmium-zinc-telluride which, in turn, is mounted upon an electrically insulative mounting disk 312 formed, for example, of alumina, and across the midpoint of which is a notch 314 which supports a small circuit board 316 in cantilever fashion. Circuit board 316 is in electrical communication with both the forward and rear surfaces of detector crystal 310 through printed circuitry supported by the disk 312 which, inter alia, communicates with the forward face of crystal detector 310 to provide instrument ground thereto via a grounding wire 318. Circuit board 316 functions to support the integrator stage 108 of the preamplifier function described in connection with FIG. 3A. Next in the sequence of components is a crystal mount 320 which is formed, for example, of tungsten to provide for the attenuation of radiation impinging toward the sides of the detector component. Mount 320 is necked down at 322 to receive the corresponding forward portion 306 of shield 298. The forward edge 324 of mount 320 is grooved to receive and support a disk-shaped conductive window 326 through which radiation may pass. A press fit serves to support window 326. Lastly, the earlier-described foamaceous cushion 264 is revealed.

Figure 16:
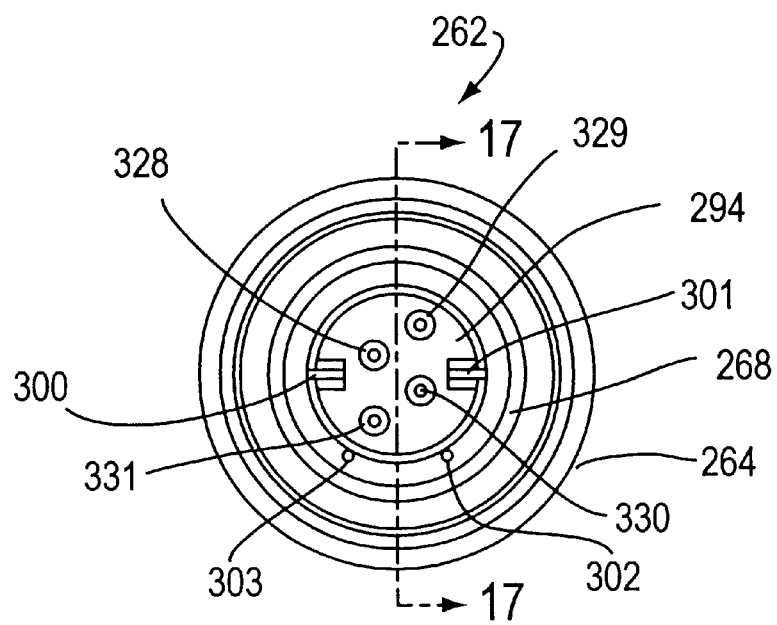
FIG. 16 is an end view of the assembly show in FIG. 14.

Turning to FIG. 16, a rear view of the assembly 262 is provided. In the figure, leads extending from the circuit board 316 are shown at 328–331. Additionally, the instrument ground connections with wires 300 and 301 are shown, those wires being bent over against an appropriate terminal formed within the cap 294.

Figure 17:
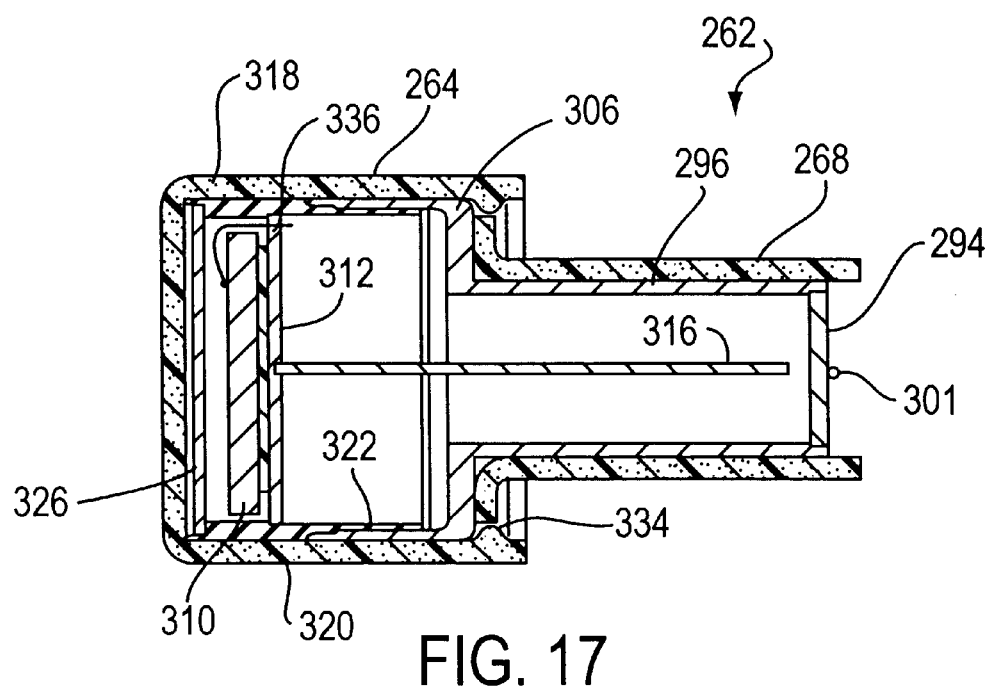
FIG. 17 is a sectional view taken through the plane 17—17 shown in FIG. 16.

FIG. 17 is a cross-section of the assemblage 262. In the figure, an annular lip 334 is seen to be formed just beyond the opening of the cushion 264. This lip nests over the rear corner of shield forward portion 306. The figure further reveals that the crystal detector 310 is retained against mounting disk 312 with a conductive adhesive represented at 336. In general, in the course of final assembly, the region behind mounting disk 312 is potted.

Figure 18:
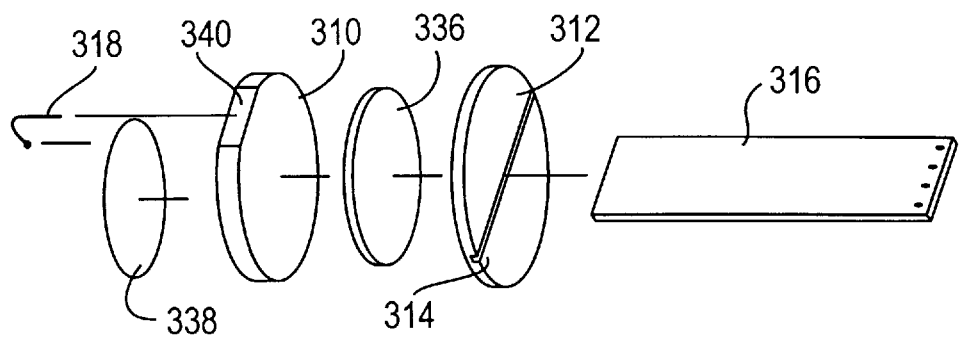
FIG. 18 is an exploded view of the detector crystal, support and printed circuit board assembly shown in FIG. 15.
Figure 19:
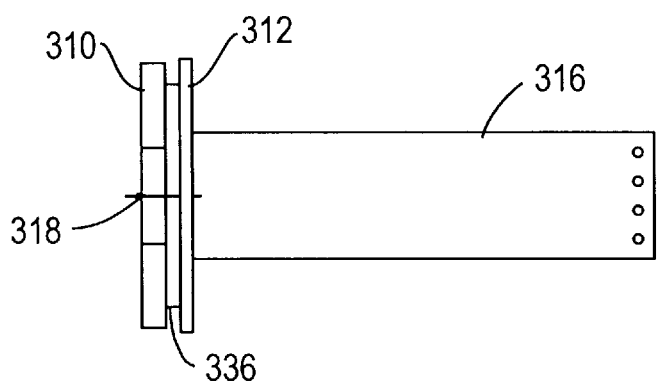
FIG. 19 is a top view of the assembly of FIG. 18.
Figure 20:
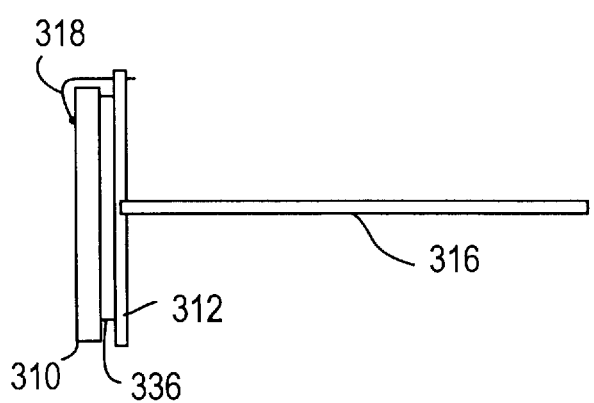
FIG. 20 is a side view of the assembly of FIG. 19.
Figure 21:
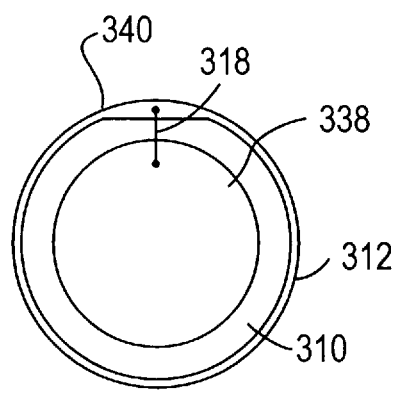
FIG. 21 is a front view of the assembly of FIG. 20.

Looking to FIG. 18, the sub-assembly of mounting disk 312, circuit board 316, adhesive 336, and detector crystal 310 is revealed. Note that the crystal detector is configured having a cord-shaped portion removed at 340 to gain access for the ground wire 318. For the instant embodiment wherein the size of the detector crystal 310 is about 15 mm in diameter, a very thin brass foil 338 is adhered to the forward surface of crystal 340 to implement the application of electrical ground thereto. This brass foil 338 is seen again in FIG. 21, FIGS. 19 through 21 showing the completed crystal detector sub-assembly.

Figure 22:
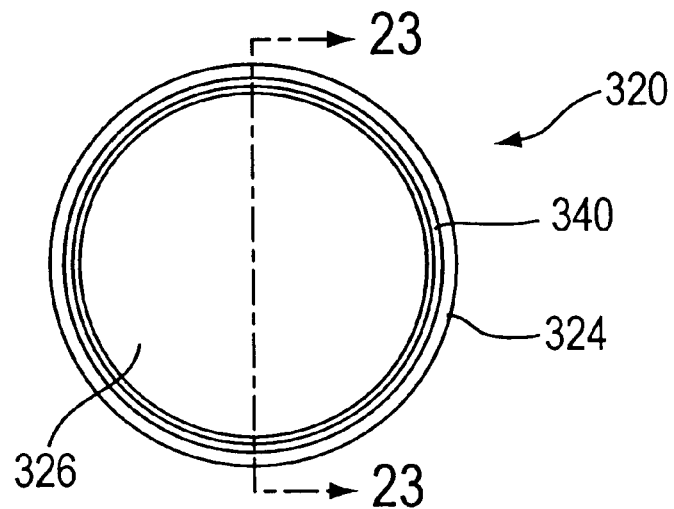
FIG. 22 is a front view of a detector mount shown in FIG. 15.
Figure 23:
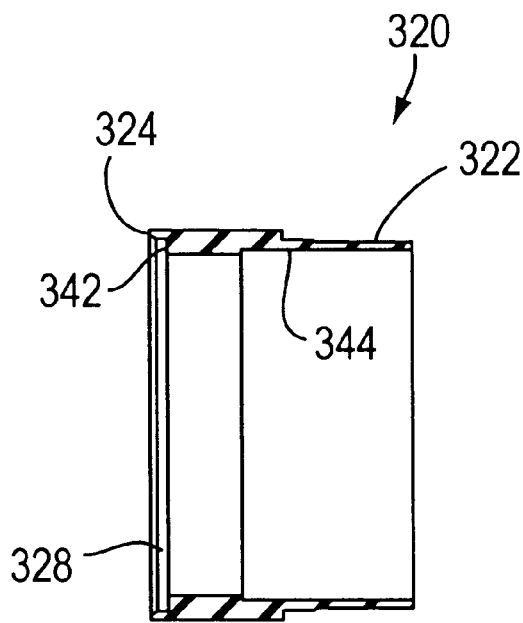
FIG. 23 is a sectional view taken through the plane 23—23 shown in FIG. 22.

FIGS. 22 and 23 reveal the structure of the detector mount 320 and the window 326, which is supported by it. FIG. 23 reveals the annular recess 342 within which the disk-shaped window 326 is press fitted. Additionally, an annular ledge 344 is formed internally within this tungsten component so as to receive the mounting disk 312.

Referring to FIG. 24, the disposable handle component 72 discussed generally in connection with FIG. 1 is revealed in pictorial fashion. The handle component 72 includes a handle housing represented generally at 360 having a forwardly disposed retainer portion represented generally at 362 which extends inwardly from a contact positioning surface 364 which functions as a forwardly disposed cam surface. This cam surface will be one component defining the abutting line 74 shown in FIG. 1. The orientation ridge 78 is shown at the top of the handle housing 360 and the cable relief component again is seen along with cable 22 extending to a plug connector 18.

Looking additionally to FIG. 25, an exploded view of a disposable handle component 72 is provided which, initially, reveals that few parts are involved in its structuring. In this regard, the handle housing 360 is shown to be formed in two mating halves 360a and 360b. Halves 360a and 360b include an end wall represented generally at 366 which is formed of housing end wall halves 366a and 366b. These end wall halves engage the elastomeric cable relief component 76 surmounting flexible cable 22. Flexible cable 22 extends forwardly within the handle housing 360 as represented at 368 to be connected into a combined electrical contact assembly and sealing assembly represented generally at 370. Additional cable relief with respect to the cable portion 368 is provided by a holding thereof as represented at 372. Assembly 370 is mounted within the handle housing 360 by an arrangement including three alignment ears, two of which are revealed at 374 and 376 which are engaged within a rib structure extending inwardly from each housing half 360a and 360b. One such rib assemblage is seen at 378a. Assembly 370 has a forwardly disposed opening (not shown) which confronts a cylindrical receiving cavity defined by a forwardly disposed insert member represented generally at 380. Insert member 380 additionally supports a thumb latch 382 which is outwardly biased from the housing handle 360 by a coil spring 384. Looking additionally to FIGS. 26 and 27, it may be observed that the thumb latch 382 extends normally outwardly from the contact positioning surface or cam surface 364 when the handle component 72 is not connected to the detector component 70. These figures also show the handle housing 360 being disposed about a longitudinal handle housing axis 386.

Looking to FIG. 28, a left side view of the handle component 72 is revealed. In the figure, the handle housing 360 is revealed at the retainer portion 362. Note that the insert member 380 is mounted between housing halves 360a and 360b. The outer cylindrical wall of the insert member 380 defines a cylindrical cavity 390. Extending along the length of cavity 390 are two guideways, a principal guideway 392 and a second guideway 394. Confronting the receiving cavity 390 is the electrical contact and sealing assemblage 370. In this view, the electrical contact assembly terminals are revealed in general at 396 along with an integrally molded elastomeric ring seal 398. Note that the electrical assembly terminals 396 are in a pattern of five terminals which corresponds with the five electrical terminals described in connection with positioning post 236 in FIG. 11. While the discrete electrical contact surfaces at support surface 238 are non-resilient and flat, the corresponding contacts or terminals 396 are resilient and each is canted in a direction which will be seen to be the direction of orientation movement of the positioning shaft 236. FIG. 28 additionally reveals that the width wise extent of the guideway 392 corresponds with the widthwise extent of orientation boss 240, while the widthwise extent of guideway 394 corresponds with the widthwise extent of orientation boss 242. Those widthwise extents are such as to permit the slideable insertion of the orientation bosses therewithin as the positioning shaft 236 moves into the cylindrical receiving cavity 390. As it is so inserted, the tip region thereof will be engaged by the annular elastomeric ring seal 398 to protect the engaging electrical components.

Figure 29A:
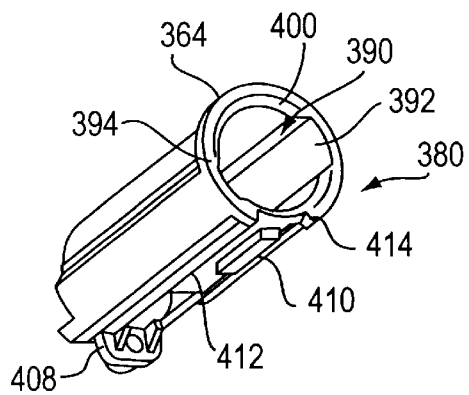
FIG. 29A is a perspective view of an insert member employed with the handle component of FIG. 28, showing the forwardly disposed portions thereof.

Looking to FIG. 29A, insert member 380 is revealed in perspective detail. In the figure, the contact positioning or forwardly disposed cam surface 464 is revealed. Note that the surface is beveled at 400 to facilitate the insertion of the positioning shaft 236. Guideways 392 and 394 are seen extending through the receiving cavity 390. FIG. 25 reveals the structuring of the member 380 to slideably support the thumb latch 382 and its associated coil spring 384. In this regard, looking additionally to FIGS. 30A and 30B, the latch 382 is configured having a keyway 402 of rectangular cross-section and a rearwardly extending post 404 over which spring 384 is mounted. The forward portion of spring 384 abuts against a rear face 406 of the latch 382. FIG. 29A shows the inward or rear support 408 for receiving the post 404 and a rectangular key 410 for slideable insertion within keyway 402. Guide surfaces 412 and 414 guide the sides of the latch 382. With the arrangement, the latch is forwardly biased such that, in an unlatched state, its tip extends outwardly from the contact surface 364 a short distance such that it ultimately is received within the latching notch 284 of support portion 228 of the detector component.

Figure 29B:
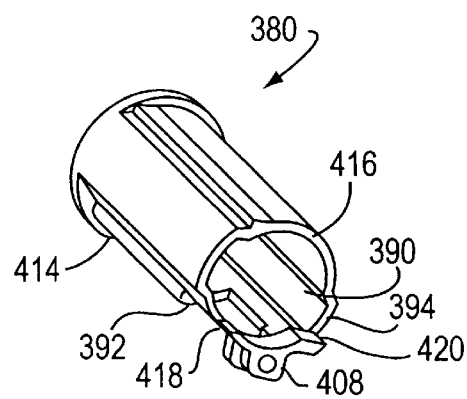
FIG. 29B is a perspective view of the handle component of FIG. 29A showing the rearwardly disposed portions thereof.

FIG. 29B provides a pictorial representation of the opposite side of the insert member 380. The figure reveals that the guideways 392 and 394 extend through the cylindrical receiving cavity 390 and emerge at a rearward or inwardly disposed cam surface 416. Also located interrupting the inwardly disposed cam surface 416 is an operational orientation stop component or surface 418 and a fully inserted orientation stop component 420 which functions to facilitate the removal of the positioning shaft 236 following usage of the system.

In the course of setting up the system 10, the practitioner will grasp a cleaned and sterilized detector component 70 and unpackage a sterile disposable handle 72 with its associated cable 22. The rearward portion of positioning shaft 236 then is inserted within the receiving cavity 390 until the lower cam follower surface 246 of orientation boss 240 engages the forwardly disposed cam surface 364. As discussed in connection with FIGS. 4 and 5, the widthwise extent of the orientation boss 240 is greater than that of orientation boss 242 and the cam follower surface 246 is rearwardly disposed with respect to the corresponding cam follower surface 250. Thus, the wider surface 246 slides along forward cam surface 364 until it encounters guideway 392. Should that follower surface 246 encounter the smaller guideway 394, it will merely slide across it. When the orientation boss 246 commences to be slideably inserted within the guideway 392, the orientation boss 242 will be aligned with guideway 394 and slide directly therewithin.

Figure 31A:
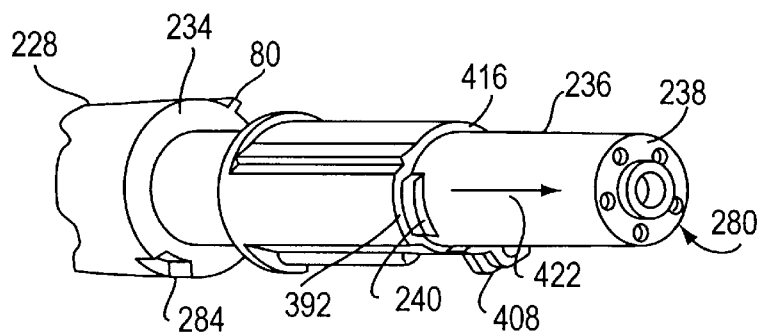
FIG. 31A is a pictorial view showing the insertion of a positioning shaft within the insert member of FIGS. 29A and 29B.
Figure 30A:
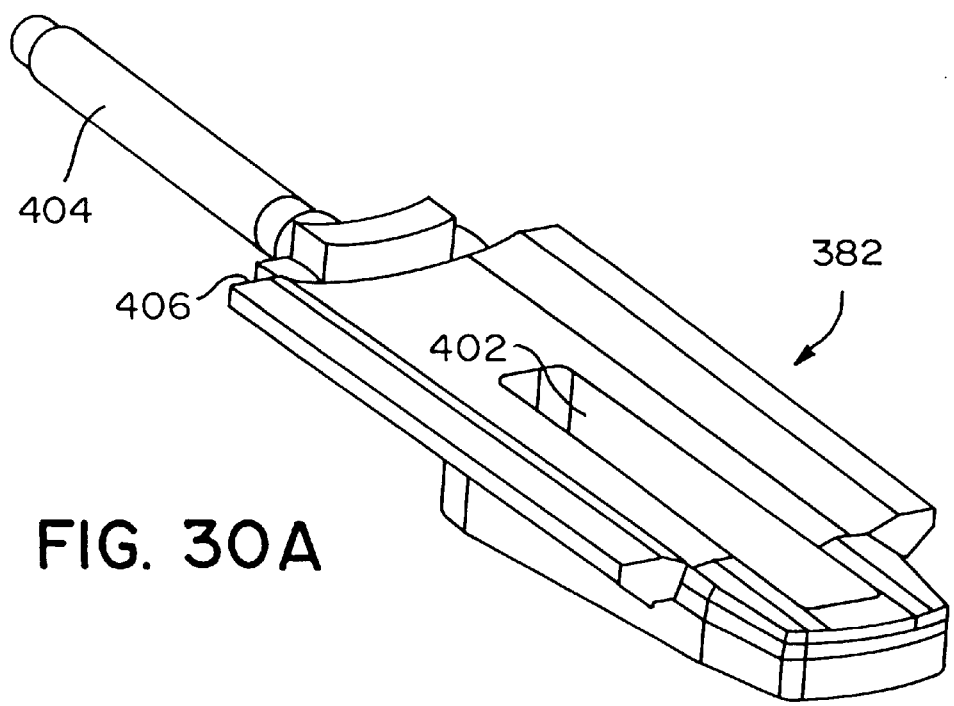
FIG. 30A is a perspective view of a latch employed with the handle component of FIG. 28, showing inwardly disposed portions thereof.
Figure 30B:
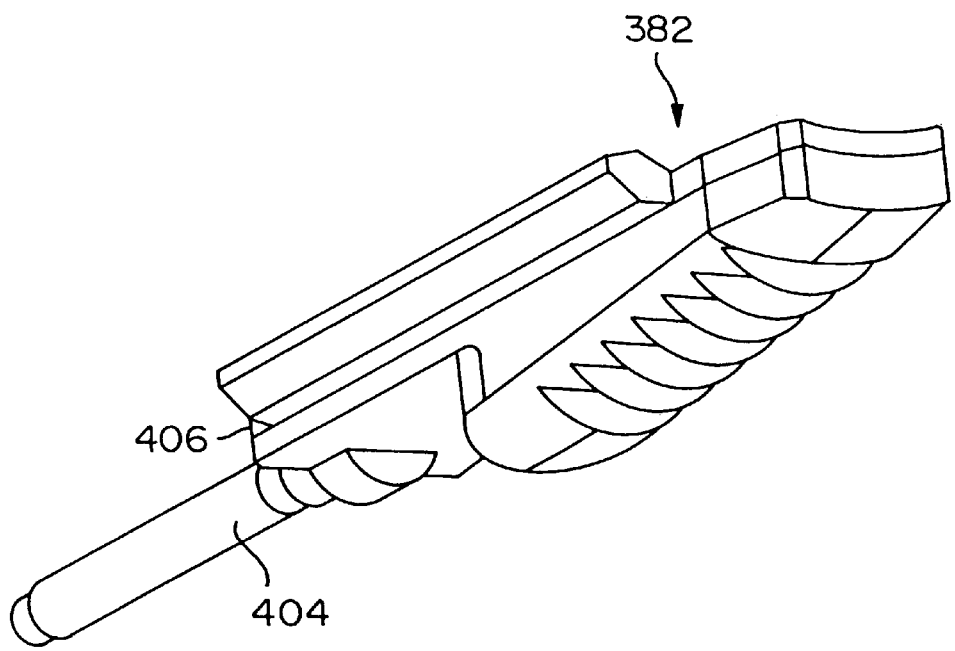
FIG. 30B is a perspective view of the latch of FIG. 30A showing the outwardly disposed portions thereof.

Referring to FIG. 31A, this slideable movement of the positioning shaft 236 continues in the direction represented by arrow 422 in general until the contact positioning surface 234 of support portion 228 of the detector component 70 contacts the contact positioning or cam surface 364. The positioning shaft 236 then will be at a fully inserted orientation and surface 234 will have caused a retraction of the extended tip of thumb latch 382. FIG. 30A shows the guide boss 240 as it is emerging from guideway 392. In this guideway controlled orientation, the five flat and discrete electrical contact surfaces 280 have an initial insertion orientation as they confront the resilient contact terminals 396 (FIG. 28) and initial contact between these two matched terminal assemblies will be made at this insertion orientation. However, it is a benign contact, in that no damage will be done to the system in the event the system will have been turned on from on-off switch 30 prior to the insertion procedure. In this regard, assigning electrical functions to the contacts looking rearwardly from the forward end of the probe assembly, and starting from the top contact or terminal in considering them in a clockwise arrangement, the uppermost contact is coupled with the shielding components. The next contact carries a bias. The next contact is one carrying circuit power. The next contact carries the signal from the detector and preamplifier, and the final fifth contact is a common. With the arrangement of the orientation boss 392 and the stop surface 418, during the full insertion procedure, the bias component of the detector 70 will contact the shield terminal of the handle 72. The power contact of the detector 70 will contact the bias component of the handle 72. The signal contact of the detector component 70 will contact the handle 72 power terminal. The common contact of detector 70 will contact the signal terminal of the handle component 72, and the shield contact of the detector 70 will contact the common terminal of the handle component 72. Upon insertion into an operational orientation, the contacts will align in proper correspondence.

Figure 31B:
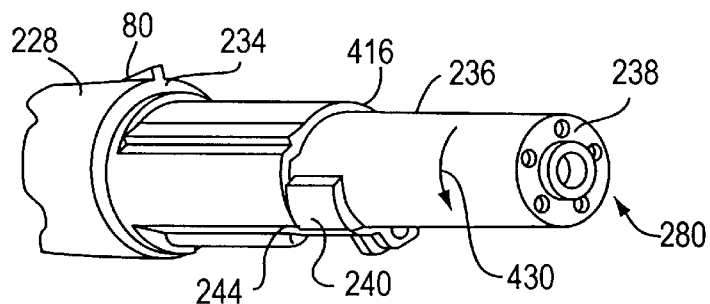
FIG. 31B is a pictorial representation showing the rotational movement involved in positioning the detector component of the invention in an operational orientation within the handle component.
Figure 32:
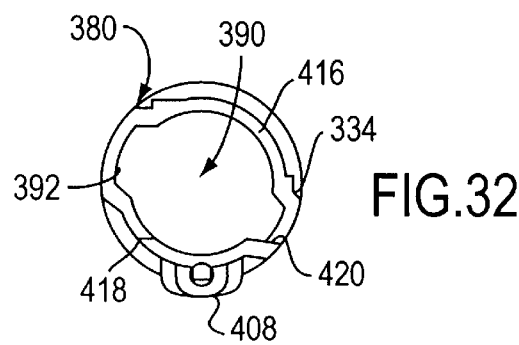
FIG. 32 is a rear end view of the insert component of FIG. 29B.

Referring to FIG. 31B, the procedure of alignment to operational orientation is represented. In this regard, the positioning shaft 236 is rotated as represented by arrow 430. As this occurs, the upper cain follower surface 244 of orientation boss 240 slides along the inward cam surface 416 until it encounters stop component 418. Simultaneously, the corresponding upper cam surface 248 of orientation boss 242 also slides upon the inward cam surface 416. Thus, the dynamic balance of the positioning shaft 236 is enhanced. As the orientation boss 240 encounters stop member 418, the smooth electrical contact surfaces 280 are aligned and in contact with the proper resilient terminals 396 of the handle component 72. During this same rotation as represented at arrow 430, the retracted tip of thumb latch 382 rides against contact positioning surface 234 of supporting component 228. This tip of the latch reaches latching notch 284 just as the orientation boss 240 makes contact with stop component surface 418. The latch then moves forwardly under the bias of spring 384 to complete the latching maneuver.

To remove the detector component 70 from the disposable handle 72, the thumb latch 382 is retracted by thumb movement such that its tip is removed from latching notch 284 and the detector component 70 and its associated positioning shaft 236 is rotated in a sense opposite arrow 430 until orientation boss 242 makes contact with the surface of stop component 420. At this position, orientation boss 240 is aligned with guideway 392 and orientation boss 242 is aligned with guideway 394. The detector component 70 then is easily removed, whereupon the handle component 72 is discarded and the detector component 70 is cleaned and sterilized for reuse.

Figure 33:
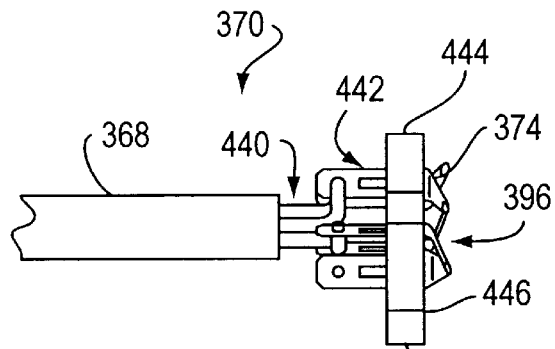
FIG. 33 is a side view of an electrical contact assemblage employed with the handle component of the invention.
Figure 34:
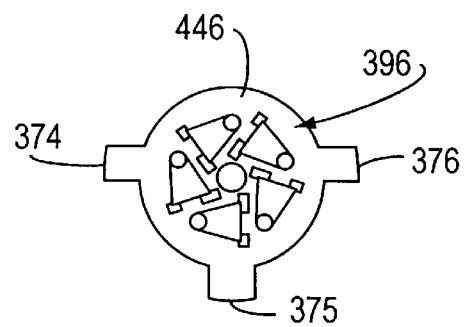
FIG. 34 is a front view of the contact assemblage of FIG. 32.

Now considering the structuring of the electrical contact assembly and sealing assembly 70, reference is made to FIG. 33 wherein the contact assemblage component are revealed. In the figure, cable component 368 is seen extending such that its five electrical components represented generally at 440 may be coupled with appropriate ones of the rearwardly extending blade portions shown generally at 442 of the resilient terminals 396. These terminals each extend through a rigid, electric insulative terminal support board 444 within which are formed the earlier-described supporting ears 374 and 376 as well as a downwardly depending ear 375. It may be noted that the individual resilient terminals and the pattern thereof 396 are bent over at the confronting surface 446 in a direction corresponding with earlier-described arrow 430 (FIG. 31B). FIG. 34 reveals the pattern and it may be noted that each of the terminals of the pattern 396 terminate in a contact hemisphere to enhance the electrical contact between each of them and the contact surfaces 280 (FIG. 31B).

Figure 35A:
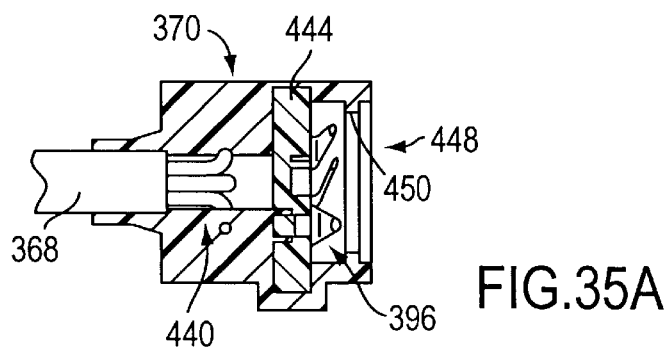
FIG. 35A is a sectional view of a sealing assembly incorporating the assemblage of FIGS. 33 and 34.
Figure 35B:
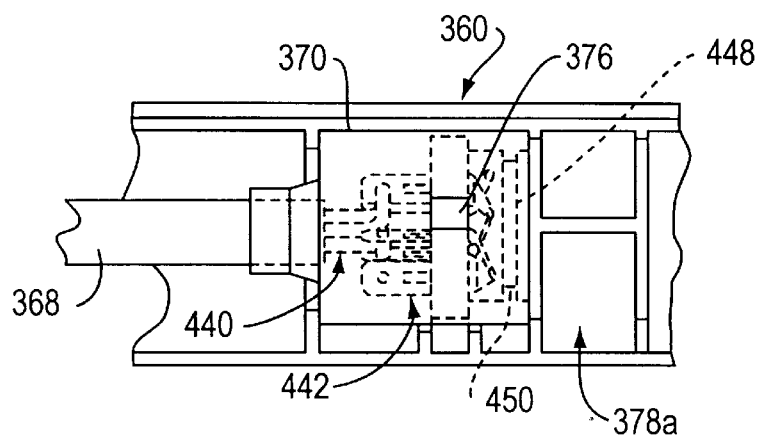
FIG. 35B is a partial sectional view of the handle component of the invention showing the sealing assembly of FIG. 35A.

Turning to FIGS. 35A and 35B, it may be observed that the terminal support board 444 and its associated cable component 368 is insert molded with an elastomeric polymer to provide the sealing assembly and contact assemblage 370. This molding procedure provides for the provision of an open, forwardly facing cavity 448 having therein an integrally formed annular O-ring seal shown in phantom at 450. Seal 450 engages the smooth rearward tip portion of positioning shaft 236 during the above-described insertion procedure. Thus, the contacts 280 and 396 are fully protected during the operational union of detector component 70 with handle component 72.

Turning to FIG. 36, the operational orientation of the detector component 70 within the handle component 72 is revealed. Note that the contact support surface 238 of the positioning shaft 236 has entered the sealing assembly and electrical contact assemblage 370 and the forward tip of thumb latch 382 has moved into the latching notch 284. The abutment line 74 thus is established. FIG. 35 further reveals that the handle housing 360 is configured to incorporate cable relief ribs represented generally at 452 which aid in forming the folded cable relief 372.

Figure 37:
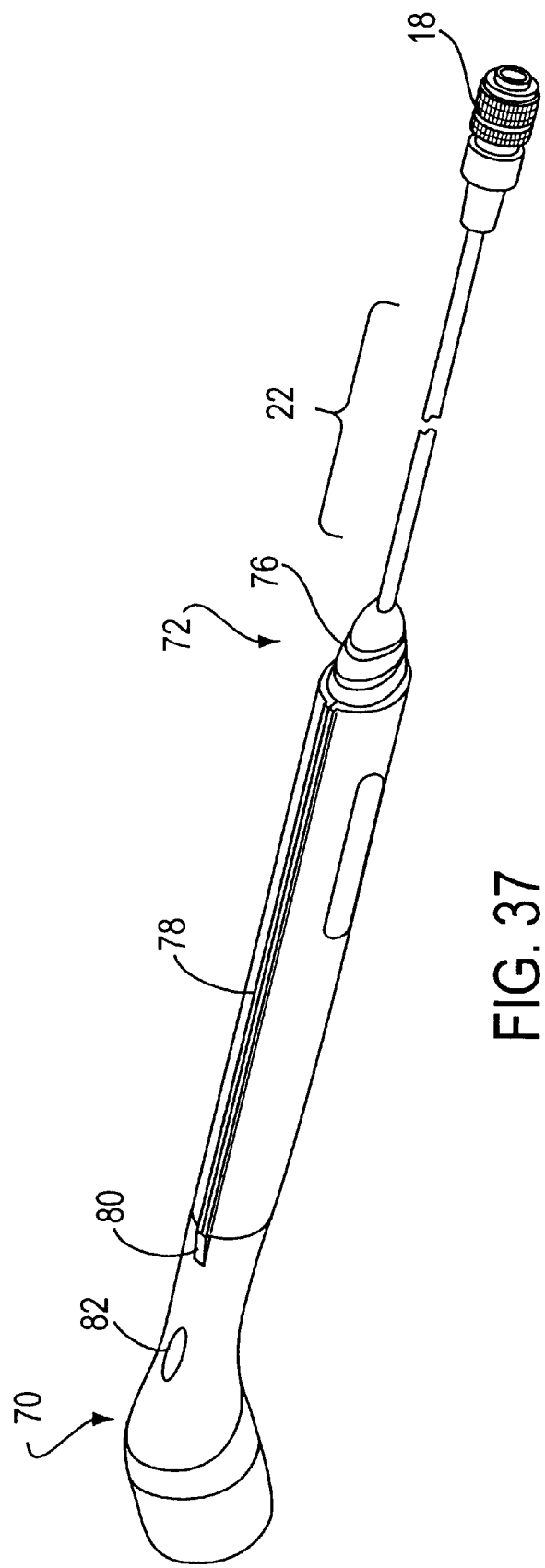
FIG. 37 is a pictorial view of the united handle and detector components of FIG. 36.
Figure 38:
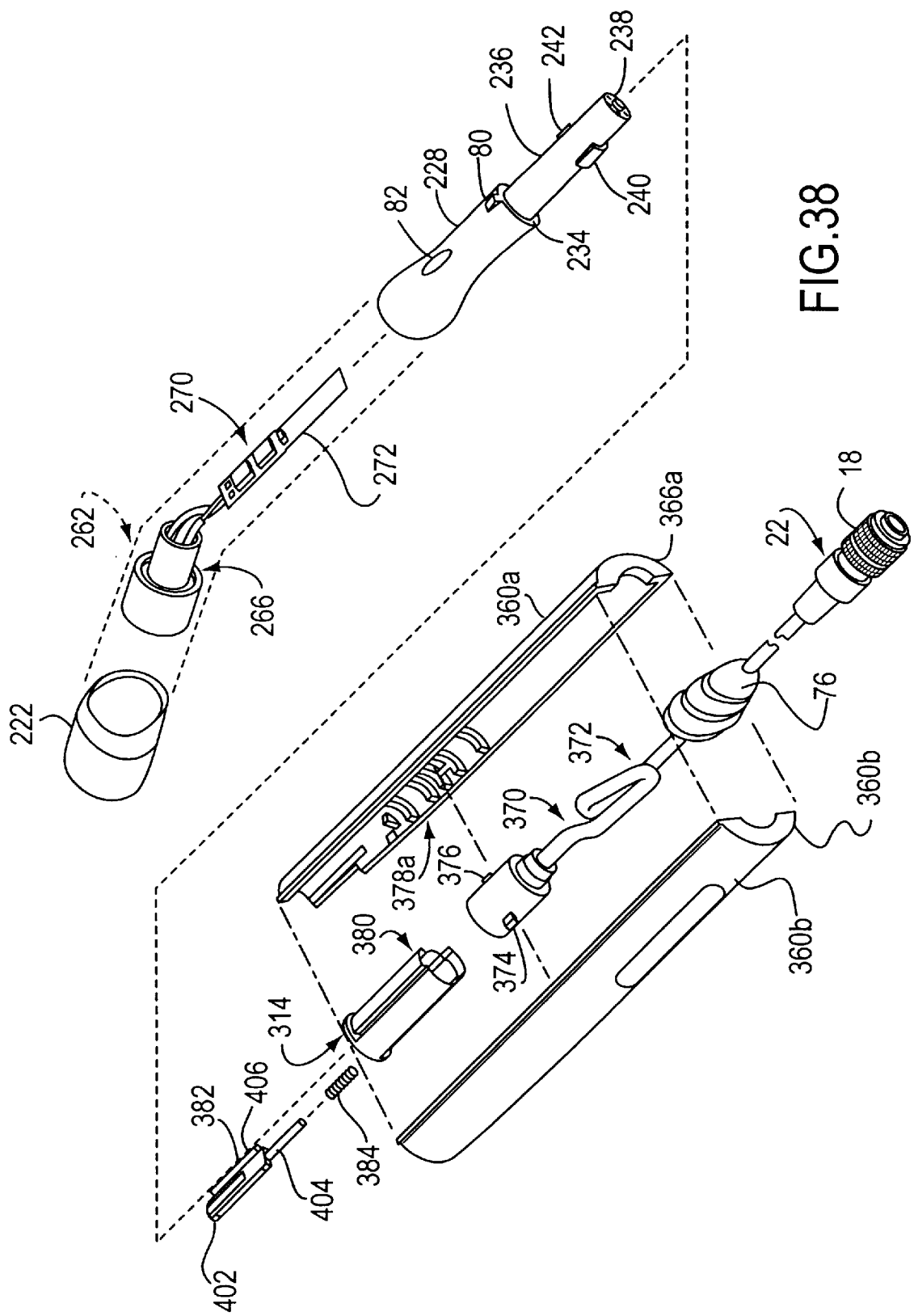
FIG. 38 is an exploded view showing both the handle component and detector component assembly.

The assembled handle and detector components are pictured in their operational orientations in FIG. 37. This assembly of FIG. 37 is shown in exploded fashion in FIG. 37.

Since certain changes may be made in the above system and apparatus without departing from the scope of the invention herein involved, it is intended that all matter contained in the above description or shown in the accompanying drawings shall be interpreted as illustrative and not in a limiting sense.

We claim:

1. An instrument for detecting and locating sources of radiation emissions, comprising:
    a first housing including:
    a detector mount portion extending from a window portion,
    a support portion extending from said detector mount portion to a first contact
    a positioning shaft extending from said support portion along a shaft axis to an electrical contact support surface,
    a radiation detector assembly within said mount portion responsive to said radiation emissions for providing a detector output,
    a treatment circuit mounted within said support portion responsive to said detector output for providing output signals corresponding with said detector output,
    first and second shaft electrical contacts mounted upon said electrical contact support surface and electrically coupled with said treatment circuit, and
    first orientation boss positioned upon said positioning shaft; and
    a second housing including:
    a forward retainer portion having a second contact positioning surface, a receiving cavity extending inwardly along a housing axis, having a first guideway for slideably receiving said first orientation boss,
    an electrical contact support mounted in confronting relationship with said receiving cavity, first and second housing electrical contacts supported upon said electrical contact support and oriented to engage respective said first and second shaft electrical contacts and said first contact positioning surface being in freely mutually abutting contact with said second contact positioning surface when said positioning shaft is fully inserted within said receiving cavity, and a flexible cable having first and second lead components electrically coupled with respective said first and second housing electrical contacts.

2. The instrument of claim 1 in which:

said positioning shaft is cylindrical;

said second housing receiving cavity is cylindrical; and including at least one annular seal component located within said second housing extending about said electrical contact support and outwardly of said first and second electrical contacts, said seal having a peripheral configuration for slideably, sealingly engaging said positioning shaft when said positioning shaft is located within said receiving cavity.

3. The instrument of claim 2 in which:

said second housing is formed of polymeric material; and said seal component includes an annular ring integrally formed therewith for engaging said positioning shaft.

4. The instrument of claim 1 in which:

said first orientation boss is positioned upon said positioning shaft a predetermined shaft distance along said shaft axis from said electrical contact support surface;

said second housing forward retainer portion receiving cavity extends inwardly along said housing axis to an annular receiving cam extending circumferentially about said housing axis to a positioning stop; and said second housing electrical contact support is mounted inwardly along said housing axis from said annular receiving cam a distance substantially corresponding with said predetermined shaft distance.

5. The instrument of claim 4 in which said first and second housing electrical contacts are oriented to engage respective said first and second shaft electrical contacts when said positioning shaft is inserted within said receiving cavity and rotated to position said first orientation boss in abutment against said positioning stop.

6. The instrument of claim 4 in which:

said first housing detector mount portion extends along a detector axis, said support portion extends along a support axis co-axial with said shaft axis, said detector axis is canted with respect to said support axis and lies within a plane common with said support axis and said shaft axis, said plane defining an orienting location at said first housing and at said second housing when said orientation boss is in said abutment against said positioning stop;

said second housing including an upstanding orientation ridge positioned at said orientation location for providing a tactile instrument orientation cue.

7. The instrument of claim 6 including a thumb rest surface formed within said first housing support portion at said orientation location, said surface lying within a surface plane at least a portion of which is substantially perpendicular to said common plane, for providing a tactile instrument orientation cue.

8. An instrument system for detecting and locating sources of radiation emission, comprising:

a sterilizable detector component including:

a detector housing including a forward portion extending along a detector axis to a forward surface and a support portion extending therefrom along a support axis including a cylindrical positioning shaft extending from said support portion to an electrical contact support surface;

a crystal mount positioned within said detector housing forward portion and having a radiation transmitting opening adjacent said forward surface, a radiation transmissible window positioned at said forward surface;

a crystal detector positioned upon said crystal mount, said crystal detector having a forward surface facing said radiation transmitting opening and an oppositely disposed rearward surface and responsive to radiation passing through said window to provide a detector output, a treatment circuit located within said support portion having an input in adjacency with said crystal detector for response to and electrically treating said detector output to provide output signals corresponding therewith;

an electrical terminal assemblage having a predetermined pattern of discrete electrical contact surfaces mounted at said contact support surface, said electrical contact surfaces being in electrical communication with said treatment circuit, and a first orientation boss located upon said positioning shaft at a predetermined location, having a first circumferential widthwise extent and having a first upper cam follower surface and an oppositely disposed first lower cam follower surface;

said system further including a handle component comprising:

a hand gripable handle housing disposed about a handle axis;

a retainer portion forwardly disposed upon said handle housing, having a forwardly disposed cam surface and a generally cylindrical receiving cavity configured to slideably receive said positioning shaft and extending inwardly from said forwardly disposed cam surface a cavity length to an inwardly disposed cam surface, a first guideway extending between said forwardly disposed cam surface and said inwardly disposed cam surface, said first guideway being located adjacent said receiving cavity at a predetermined location and having a widthwise extent for slideably receiving said first orientation boss in guiding relationship when said positioning shaft is inserted within said receiving cavity, said first lower cam follower surface being movable upon said forwardly disposed cam surface to locate said first orientation boss within said first guideway for movement therealong to a fully inserted orientation of said positioning shaft suited for subsequent rotational movement of said first orientation boss first upper cam follower surface upon said inwardly disposed cam surface to an operational orientation, a first stop component engageable with said first orientation boss when said positioning shaft is at said operational orientation;

an electrical contact assemblage aligned with and confronting said receiving cavity having a pattern of discrete electrical contacts arranged in correspondence with said predetermined pattern of discrete electrical contact surfaces and engageable in circuit completing relationship with said electrical contact surfaces when said first orientation boss is in said operational orientation, an elongate flexible cable having leads connected in electrical association with said electrical contacts, and a sealing assembly extending about said electrical contact assemblage and engageable in sealing relationship with said positioning shaft when said positioning shaft is moved into said fully inserted orientation.

9. The instrument of claim 8 in which said first stop component is integrally formed with said insert member.

10. The instrument of claim 8 in which said handle component includes a second stop engageable with said second orientation boss when said positioning shaft is in said fully inserted orientation and said second orientation boss is aligned with said second guideway.

11. The instrument of claim 10 in which said first circumferential widthwise extent of said first orientation boss is greater than the circumferential widthwise extent of said second orientation boss.

12. The instrument of claim 10 in which said second orientation boss includes a second lower cam follower surface at a location spaced upwardly from the location of said first lower cam follower surface a distance effective to space said second lower cam follower surface from said upper cam surface when said first lower cam follower surface is moved thereupon.

13. The instrument of claim 8 in which:

said sealing assembly is formed of an elastomeric material molded in sealing relationship over said flexible cable leads at their connection with said electrical contacts of said electrical contact assemblage.

14. The instrument of claim 13 in which said sealing assemblage includes an integrally formed ring seal spaced from said electrical contact assemblage discrete electrical contacts and sealingly engageable with said positioning shaft.

15. The instrument of claim 8 in which:

said detector housing forward portion detector axis is canted with respect to said support axis and lies in a plane common with said support axis, said plane defining an orienting location at said detector housing and at said hand gripable handle housing when said positioning shaft is in said fully inserted orientation and said first orientation boss first upper cam follower surface is in said operational orientation; and said hand gripable handle housing includes an upstanding orientation ridge positioned at said orientation location for providing a tactile instrumentation orientation cue.

16. The instrument of claim 15 including a thumb rest surface formed within said detector housing support portion at said orientation location, lying within a surface plane at least a portion of which is substantially perpendicular to said common plane, for providing a tactile instrument orientation cue.

17. The instrument of claim 8 in which:

said crystal mount is configured as a tube; and said crystal detector forward surface is spaced inwardly from said window a distance selected to collimate said radiation passing through said window.

18. A surgical system for detecting and locating sources of radiation emission emanating from tissue of a body, comprising:

a sterilizable detector component, comprising:

a detector housing including a forward portion extending along a detector axis to a forward window through which said radiation emission is transmissible, and a support portion extending from said forward portion and including a positioning shaft extending a predetermined length outwardly from said support portion, a crystal mount positioned within said detector housing forward portion;

a crystal detector positioned upon said crystal mount, said detector having a forward surface adjacent said window and an oppositely disposed rearward surface and responsive to radiation passing through said window to provide a detector output, a treatment circuit within said detector housing, responsive to said detector output to provide output signals corresponding therewith, and an electrical terminal assemblage mounted upon said positioning shaft and in electrical communication with said treatment circuit;

a disposable handle component, including:

a hand gripable handle housing having a forwardly disposed retainer portion with a receiving cavity configured for removably receiving said positioning shaft to locate it at an operative orientation, an electrical contact assemblage mounted within said handle housing adjacent said receiving cavity and having electrical contacts mounted thereon engageable in circuit completing relationship with said electrical terminal assemblage when said positioning shaft is in said operative orientation, a flexible electrical transmission cable coupled to said handle housing and having electrical leads connected with electrical contact assemblage electrical contacts and extending to an electrical connector component;

said handle housing including a sealing assembly extending about said electrical contact assemblage and engageable in sealing relationship with said positioning shaft when in said operative orientation; and a signal treatment and control assembly having an input connector for removable electrical coupling with said cable electrical connector component and responsive to said output signals conveyed by said cable to provide perceptible output signals.

19. The surgical system of claim 18 in which:

said detector housing support portion extends from said forward portion to a first contact surface;

said positioning shaft extends outwardly from said first contact surface, is cylindrical and includes a first orientation boss extending therefrom at a predetermined location, having a first widthwise extent, a first upper arm cam follower surface and an oppositely disposed first lower cam follower surface;

said handle housing includes a forwardly disposed second contact surface and said retainer portion includes a first guideway extending along said receiving cavity between said second contact surface and an inwardly disposed cam surface;

said positioning shaft is locatable at said operative orientation when said first contact surface is in abutting adjacency with said second contact surface; and said first guideway having a widthwise extent for slideably receiving said first orientation boss in guiding relationship when said positioning shaft is inserted within said receiving cavity.

20. The surgical system of claim 19 in which said first lower cam follower surface is movable upon said second contact surface to locate said first orientation boss within said first guideway for movement therealong to a fully inserted orientation of said positioning shaft suited for subsequent rotational movement of said first orientation boss first upper cam follower surface upon said inwardly disposed cam surface to said operative orientation.

21. The surgical system of claim 20 in which said handle housing retainer portion includes a first stop component engageable with said first orientation boss when said positioning shaft is at said operative orientation.

22. The surgical system of claim 10 in which said second orientation boss includes a second lower cam follower surface at a location spaced upwardly from the location of said first lower cam follower surface a distance effective to space said second lower cam follower surface from said second contact surface when said first lower cam follower surface is moved thereupon.

23. The surgical system of claim 22 in which said first orientation boss first widthwise extent is greater than the widthwise extent of said second orientation boss.

24. An instrument for detecting and locating sources of radiation emissions, comprising:

a first housing including:

a detector mount portion extending from a window portion, a support portion extending from said detector mount portion to a first contact positioning surface and including a latching notch extending from said first contact positioning surface, a positioning shaft extending along a shaft axis from said first contact positioning surface to an electrical contact support surface, a radiation detector assembly within said mount portion responsive to said radiation emissions for providing a detector output, a treatment circuit mounted within said support portion responsive to said detector output for providing output signals corresponding with said detector output, first and second shaft electrical contacts mounted upon said electrical contact support surface and electrically coupled with said treatment circuit, and a first orientation boss positioned upon said positioning shaft a predetermined shaft distance along said shaft axis from said electrical contact support surface; and a second housing including:

a forward retainer portion having a receiving cavity extending inwardly along a housing axis to an annular receiving cam extending circumferentially about said housing axis to a positioning stop and having a first guideway for slideably receiving said first orientation boss, said forward retainer portion including a second contact positioning surface, said first contact positioning surface being in mutually abutting contact with said second contact positioning surface when said positioning shaft is fully inserted within said receiving cavity, an electrical contact support mounted in confronting relationship with said receiving cavity and inwardly along said housing axis from said annular receiving cam a distance substantially corresponding with said predetermined shaft distance, first and second housing electrical contacts supported upon said electrical contact support and oriented to engage respective said first and second shaft electrical contacts when said positioning shaft is inserted within said receiving cavity, a flexible cable having first and second lead components electrically coupled with respective said first and second housing electrical contacts, a manually retractable latching component slideably mounted upon said second housing at said forward retainer portion and spring biased to move from a retracted position outwardly from said second contact positioning surface and being retained against said bias at said retracted position by abutting contact with said first contact positioning surface when said first and second contact positioning surfaces are in mutually abutting adjacency and said first orientation boss is aligned with said first guideway, and said latching component moving under said spring bias into latching insertion within said latching notch when said first orientation boss is moved into said abutment against said positioning stop.

25. An instrument system for detecting and locating sources of radiation emission, comprising:

a sterilizable detector component including:

a detector housing including a forward portion extending along a detector axis to a forward surface and a support portion extending therefrom along a support axis including a cylindrical positioning shaft extending to an electrical contact support surface, a crystal mount positioned within said detector housing forward portion and having a radiation transmitting opening adjacent said forward surface, a radiation transmissible window positioned at said forward surface, a crystal detector positioned upon said crystal mount, said crystal detector having a forward surface facing said radiation transmitting opening and an oppositely disposed rearward surface and responsive to radiation passing through said window to provide a detector output, a treatment circuit located within said support portion having an input in adjacency with said crystal detector for response to and electrically treating said detector output to provide output signals corresponding therewith, an electrical terminal assemblage having a predetermined pattern of discrete electrical contact surfaces mounted at said contact support surface, said electrical contact surfaces being in electrical communication with said treatment circuit, and a first orientation boss located upon said positioning shaft at a predetermined location, having a first circumferential widthwise extend and having a first upper cam follower surface and an oppositely disposed first lower cam follower surface;

said system further including a handle component comprising:

a hand gripable handle housing disposed about a handle axis, a retainer portion comprising an insert member forwardly disposed upon and supported by said handle housing, having an outer wall structure supporting and formed integrally with a forward disposed cam surface and a generally cylindrical receiving cavity defined by said outer wall structure configured to slideably receive said positioning shaft and extending inwardly from said forwardly disposed cam surface a cavity length to an inwardly disposed cam surface formed integrally with said outer wall structure, a first guideway extending between said forwardly disposed cam surface and said inwardly disposed cam surface, said first guideway being located adjacent said receiving cavity at a predetermined location and having a widthwise extent for slideably receiving said first orientation boss in guiding relationship when said positioning shaft is inserted within said receiving cavity, said first lower cam follower surface being moveable upon said forwardly disposed cam surface to locate said first orientation boss within said first guideway for movement therealong to a fully inserted orientation of said positioning shaft suited for subsequent rotational movement of said first orientation boss first upper cam follower surface upon said inwardly disposed cam surface to an operational orientation, a first stop component engageable with said first orientation boss when said positioning shaft is at said operational orientation, an electrical contact assemblage aligned with and confronting said receiving cavity having a pattern of discrete electrical contacts arranged in correspondence with said predetermined pattern of discrete electrical contact surfaces and engageable in circuit completing relationship with said electrical contact surfaces when said first orientation boss is in said operational orientation, an elongate flexible cable having leads connected in electrical association with said electrical contacts, and a sealing assembly extending about said electrical contact assemblage and engageable in sealing relationship with said positioning shaft when said positioning shaft is moved into said fully inserted orientation.

26. An instrument system for detecting and locating sources of radiation emission, comprising:

a sterilizable detector component including:

a detector housing including a forward portion extending along a detector axis to a forward surface and a support portion extending therefrom along a support axis including a cylindrical positioning shaft extending to an electrical contact support surface, a crystal mount positioned within said detector housing forward portion and having a radiation transmitting opening adjacent said forward surface, a radiation transmissible window positioned at said forward surface, a crystal detector positioned upon said crystal mount, said crystal detector having a forward surface facing said radiation transmitting opening and an oppositely disposed rearward surface and responsive to radiation passing through said window to provide a detector output, a treatment circuit located within said support portion having an input in adjacency with said crystal detector for response to and electrically treating said detector output to provide output signals corresponding therewith, an electrical terminal assemblage having a predetermined pattern of discrete electrical contact surfaces mounted at said contact support surface, said electrical contact surfaces being in electrical communication with said treatment circuit, a first orientation boss located upon said positioning shaft at a predetermined location, having a first circumferential widthwise extent and having a first upper cam follower surface and an oppositely disposed first lower cam follower surface, and a second orientation boss located upon said positioning shaft substantially opposite said first orientation boss and having a second upper cam follower surface at a location substantially coplanar with said first upper cam follower surface;

said system further including a handle component comprising:

a hand gripable handle housing disposed about a handle axis, a retainer portion forwardly disposed upon said handle housing, having a forwardly disposed cam surface and a generally cylindrical receiving cavity configured to slideably receive said positioning shaft and extending inwardly from said forwardly disposed cam surface a cavity length to an inwardly disposed cam surface, a first guideway extending between said forwardly disposed cam surface and said inwardly disposed cam surface, said first guideway being located adjacent said receiving cavity at a predetermined location and having a widthwise extent for slideably receiving said first orientation boss in guiding relationship when said positioning shaft is inserted within said receiving cavity, said first lower cam follower surface being movable upon said forwardly disposed cam surface to locate said first orientation boss within said first guideway for movement therealong to a fully inserted orientation of said positioning shaft suited for subsequent rotational movement of said first orientation boss first upper cam follower surface upon said inwardly disposed cam surface to an operational orientation, a first stop component engageable with said first orientation boss when said positioning shaft is at said operational orientation, an electrical contact assemblage aligned with and confronting said receiving cavity having a pattern of discrete electrical contacts arranged in correspondence with said predetermined pattern of discrete electrical contact surfaces and engageable in circuit completing relationship with said electrical contact surfaces when said first orientation boss is in said operational orientation, an elongate flexible cable having leads connected in electrical association with said electrical contacts, a sealing assembly extending about said electrical contact assemblage and engageable in sealing relationship with said positioning shaft when said positioning shaft is moved into said fully inserted orientation, said handle component retainer portion including a second guideway extending between said forwardly disposed cam surface and said inwardly disposed cam surface and located adjacent said receiving cavity substantially diametrically opposite said first guideway and having a widthwise extent for slideably receiving said second orientation boss in guiding relationship when said positioning shaft is inserted within said receiving cavity, and said second orientation boss being movable within said second guideway with said positioning shaft to said fully inserted orientation suited for subsequent rotational movement of said second orientation boss second upper cam follower surface upon said inwardly disposed cam surface simultaneously with said movement of said first upper cam follower surface upon said inwardly disposed cam surface.

27. An instrument system for detecting and locating sources of radiation emission, comprising:

a sterilizable detector component including:

a detector housing including a forward portion extending along a detector axis to a forward surface and a support portion extending therefrom along a support axis to a contact positioning surface, a latching notch extending from said contact positioning surface, said support portion including a cylindrical positioning shaft extending along said support axis from said contact positioning surface to an electrical contact support surface, a crystal mount positioned within said detector housing forward portion and having a radiation transmitting opening adjacent said forward surface, a radiation transmissible window positioned at said forward surface, a crystal detector positioned upon said crystal mount, said crystal detector having a forward surface facing said radiation transmitting opening and an oppositely disposed rearward surface and responsive to radiation passing through said window to provide a detector output, a treatment circuit located within said support portion having an input in adjacency with said crystal detector for response to and electrically treating said detector output to provide output signals corresponding therewith, an electrical terminal assemblage having a predetermined pattern of discrete electrical contact surfaces mounted at said contact support surface, said electrical contact surfaces being in electrical communication with said treatment circuit, and a first orientation boss located upon said positioning shaft at a predetermined location, having a first circumferential widthwise extent and having a first upper cam follower surface and an oppositely disposed first lower cam follower surface;

said system further including a handle component comprising:

a hand gripable handle housing disposed about a handle axis, a retainer portion forwardly disposed upon said handle housing, having a forwardly disposed cam surface and a generally cylindrical receiving cavity configured to slideably receive said positioning shaft and extending inwardly from said forwardly disposed cam surface a cavity length to an inwardly disposed cam surface, a first guideway extending between said forwardly disposed cam surface and said inwardly disposed cam surface, said first guideway being located adjacent said receiving cavity at a predetermined location and having a widthwise extent for slideably receiving said first orientation boss in guiding relationship when said positioning shaft is inserted within said receiving cavity, said first lower cam follower surface being movable upon said forwardly disposed cam surface to locate said first orientation boss within said first guideway for movement therealong to a fully inserted orientation of said positioning shaft suited for subsequent rotational movement of said first orientation boss first upper cam follower surface upon said inwardly disposed cam surface to an operational orientation, said forwardly disposed cam surface being in mutually abutting contact with said contact positioning surface when said positioning shaft is in said fully inserted orientation, a first stop component engageable with said first orientation boss when said positioning shaft is at said operational orientation, an electrical contact assemblage aligned with and confronting said receiving cavity having a pattern of discrete electrical contacts arranged in correspondence with said predetermined pattern of discrete electrical contact surfaces and engageable in circuit completing relationship with said electrical contact surfaces when said first orientation boss is in said operational orientation, an elongate flexible cable having leads connected in electrical association with said electrical contacts, a sealing assembly extending about said electrical contact assemblage and engageable in sealing relationship with said positioning shaft when said positioning shaft is moved into said fully inserted orientation, and a manually retractable latching component slideably mounted upon said handle housing at said retainer portion and spring biased to move from a retracted position outwardly from said forwardly disposed cam surface and being retained against said bias at said retracted position by abutting contact with said contact positioning surface when said positioning shaft is in said fully inserted orientation and said first orientation boss is aligned with said first guideway;

said latching component moving under said spring bias into latching insertion within said latching notch when said first orientation boss is moved to said operational orientation.

28. An instrument system for detecting and locating sources of radiation emission, comprising:

a sterilizable detector component including:

a detector housing including a forward portion extending along a detector axis to a forward surface and a support portion extending therefrom along a support axis including a cylindrical positioning shaft extending to an electrical contact support surface, a crystal mount positioned within said detector housing forward portion and having a radiation transmitting opening adjacent said forward surface, a radiation transmissible window positioned at said forward surface, a crystal detector positioned upon said crystal mount, said crystal detector having a forward surface facing said radiation transmitting opening and an oppositely disposed rearward surface and responsive to radiation passing through said window to provide a detector output, a treatment circuit located within said support portion having an input in adjacency with said crystal detector for response to and electrically treating said detector output to provide output signals corresponding therewith, an electrical terminal assemblage having a predetermined pattern of discrete electrical contact surfaces mounted at said contact support surface, said electrical contact surfaces being in electrical communication with said treatment circuit, a first orientation boss located upon said positioning shaft at a predetermined location, having a first circumferential widthwise extent and having a first upper cam follower surface and an oppositely disposed first lower cam follower surface, and a second orientation boss located upon said positioning shaft substantially opposite said first orientation boss and having a second upper cam follower surface at a location substantially coplanar with said first upper cam follower surface;

said system further including a handle component comprising:

a hand gripable handle housing disposed about a handle axis, a retainer portion forwardly disposed upon said handle housing, having a forwardly disposed cam surface and a generally cylindrical receiving cavity configured to slideably receive said positioning shaft and extending inwardly from said forwardly disposed cam surface a cavity length to an inwardly disposed cam surface, a first guideway extending between said forwardly disposed cam surface and said inwardly disposed cam surface, said first guideway being located adjacent said receiving cavity at a predetermined location and having a widthwise extent for slideably receiving said first orientation boss in guiding relationship when said positioning shaft is inserted within said receiving cavity, said first lower cam follower surface being movable upon said forwardly disposed cam surface to locate said first orientation boss within said first guideway for movement therealong to a fully inserted orientation of said positioning shaft suited for subsequent rotational movement of said first orientation boss first upper cam follower surface upon said inwardly disposed cam surface to an operational orientation, a first stop component engageable with said first orientation boss when said positioning shaft is at said operational orientation, an electrical contact assemblage aligned with and confronting said receiving cavity having a pattern of discrete electrical contacts arranged in correspondence with said predetermined pattern of discrete electrical contact surfaces and engageable in circuit completing relationship with said electrical contact surfaces when said first orientation boss is in said operational orientation, an elongate flexible cable having leads connected in electrical association with said electrical contacts, a sealing assembly extending about said electrical contact assemblage and engageable in sealing relationship with said positioning shaft when said positioning shaft is moved into said fully inserted orientation, said handle component retainer portion including a second guideway extending between said forwardly disposed cam surface and said inwardly disposed cam surface and located adjacent said receiving cavity substantially diametrically opposite said first guideway and having a widthwise extent for slideably receiving said second orientation boss in guiding relationship when said positioning shaft is inserted within said receiving cavity, said second orientation boss being movable within said second guideway with said positioning shaft to said fully inserted orientation suited for subsequent rotational movement of said second orientation boss second upper cain follower surface upon said inwardly disposed cam surface simultaneously with said movement of said first upper cam follower surface upon said inwardly disposed cam surface; and said handle component retainer portion comprising an insert member supported by said handle housing, having an outer wall structure supporting and formed integrally with said forwardly disposed cam surface, said inwardly disposed cam surface, said first guideway, said second guideway and extending said cavity length to define said cylindrical receiving cavity.

29. An instrument system for detecting and locating sources of radiation emission, comprising:

a sterilizable detector component including:

a detector housing including at forward portion extending along a detector axis to a forward surface and a support portion extending therefrom along a support axis including a cylindrical positioning shaft extending to an electrical contact support surface, a crystal mount positioned within said detector housing forward portion and having a radiation transmitting opening adjacent said forward surface, a radiation transmissible window positioned at said forward surface, a crystal detector positioned upon said crystal mount, said crystal detector having a forward surface facing said radiation transmitting opening and an oppositely disposed rearward surface and responsive to radiation passing through said window to provide a detector output, a treatment circuit located within said support portion having an input in adjacency with said crystal detector for response to and electrically treating said detector output to provide output signals corresponding therewith, an electrical terminal assemblage having a predetermined pattern of discrete, flat non-resilient electrical contact surfaces mounted at said contact support surface, said electrical contact surfaces being in electrical communication with said treatment circuit, and a first orientation boss located upon said positioning shaft at a predetermined location, having a first circumferential widthwise extent and having a first upper cam follower surface and an oppositely disposed first lower cam follower surface;

said system further including a handle component comprising:

a hand gripable handle housing disposed about a handle axis, a retainer portion forwardly disposed upon said handle housing, having a forwardly disposed cam surface and a generally cylindrical receiving cavity configured to slideably receive said positioning shaft and extending inwardly from said forwardly disposed cam surface a cavity length to an inwardly disposed cam surface, a first guideway extending between said forwardly disposed cam surface and said inwardly disposed cam surface, said first guideway being located adjacent said receiving cavity at a predetermined location and having a widthwise extent for slideably receiving said first orientation boss in guiding relationship when said positioning shaft is inserted within said receiving cavity, said first lower cam follower surface being movable upon said forwardly disposed cam surface to locate said first orientation boss within said first guideway for movement therealong to a fully inserted orientation of said positioning shaft suited for subsequent rotational movement of said first orientation boss first upper cam follower surface upon said inwardly disposed cam surface to an operational orientation, a first stop component engageable with said first orientation boss when said positioning shaft is at said operational orientation, an electrical contact assemblage aligned with and confronting said receiving cavity having a pattern of discrete upstanding resilient electrical contacts arranged in correspondence with said predetermined pattern of discrete electrical contact surfaces each of said electrical contacts being canted in the direction of rotational movement of said first orientation boss first upper cam follower surface upon said inwardly disposed cam surface toward said operational orientation such that said upstanding resilient electrical contacts are engageable in circuit completing relationship with said electrical contact surfaces when said first orientation boss is in said operational orientation, an elongate flexible cable having leads connected in electrical association with said electrical contacts, and a sealing assembly extending about said electrical contact assemblage and engageable in sealing relationship with said positioning shaft when said positioning shaft is moved into said fully inserted orientation.

30. A surgical system for detecting and locating sources of radiation emission emanating from tissue of a body, comprising:

a sterilizable detector component, comprising:

a detector housing including a forward portion extending along a detector axis to a forward window through which said radiation emission is transmissible, and a support portion extending from said forward portion to a first contact surface and including a cylindrical positioning shaft extending a predetermined length outwardly from said first contact surface, said positioning shaft including a first orientation boss extending therefrom at a predetermined location, having a first widthwise extend, a first upper cam follower surface and an oppositely disposed first lower cam follower surface, a crystal mount positioned within said detector housing forward portion, a crystal detector positioned upon said crystal mount, said detector having a forward surface adjacent said window and an oppositely disposed rearward surface and responsive to radiation passing through said window to provide a detector output, a treatment circuit within said detector housing, responsive to said detector output to provide output signals corresponding therewith, and an electrical terminal assemblage mounted upon said positioning shaft and in electrical communication with said treatment circuit;

a disposable handle component, including:

a hand gripable handle housing having a forwardly disposed second contact surface and forwardly disposed retainer portion with a receiving cavity configured for removably receiving said positioning shaft to locate it at an operative orientation when said first contact surface is in abutting adjacency with said second contact surface, said retainer portion comprising an insert member supported by said handle housing, defining said receiving cavity and having an outer wall structure supporting and formed integrally with said second contact surface, said inwardly disposed cam surface, a first guideway extending along said receiving cavity between said second contact surface and said inwardly disposed cam surface and having a widthwise extend for slideably receiving said first orientation boss in guiding relationship when said positioning shaft is inserted within said receiving cavity, said first lower cam follower surface being movable upon said second contact surface to locate said First orientation boss within said first guideway for movement therealong to a fully inserted orientation of said positioning shaft suited for subsequent rotational movement of said first orientation boss first upper cam follower surface upon said inwardly disposed cam surface to said operative orientation and a first stop component engageable with said first orientation boss when said positioning shaft is at said operative orientation, an electrical contact assemblage mounted within said handle housing adjacent said receiving cavity and having electrical contacts mounted thereon engageable in circuit completing relationship with said electrical terminal assemblage when said positioning shaft is in said operative orientation, a flexible electrical transmission cable coupled to said handle housing and having electrical leads connected with electrical contact assemblage electrical contacts and extending to an electrical connector component, a sealing assembly extending about said electrical contact assemblage and engageable in sealing relationship with said positioning shaft when in said operative orientation; and a signal treatment and control assembly having an input connector for removable electrical coupling with said cable electrical connector component and responsive to said output signals conveyed by said cable to provide perceptible output signals.

31. A surgical system for detecting and locating sources of radiation emission emanating from tissue of a body, comprising:

a sterilizable detector component, comprising:

a detector housing including a forward portion extending along a detector axis to a forward window through which said radiation emission is transmissible, and a support portion extending from said forward portion to a first contact surface and including a cylindrical positioning shaft extending a predetermined length outwardly from said first contact surface, a first orientation boss extending from said first contact surface at a predetermined location, having a first widthwise extend, a first upper cam following surface and an oppositely disposed first lower cam follower surface, a second orientation boss located on said positioning shaft substantially opposite said first orientation boss and having a second upper cam follower surface at a location substantially coplanar with said first upper cam follower surface, a crystal mount positioned within said detector housing forward portion, a crystal detector positioned upon said crystal mount, said detector having a forward surface adjacent said window and an oppositely disposed rearward surface and responsive to radiation passing through said window to provide a detector output, a treatment circuit within said detector housing, responsive to said detector output to provide output signals corresponding therewith, and an electrical terminal assemblage mounted upon said positioning shaft and in electrical communication with said treatment circuit;

a disposable handle component, including:

a handle gripable handle housing having a forwardly disposed second contact surface, a first stop component and a forwardly disposed retainer portion with a receiving cavity configured for removably receiving said positioning shaft to locate it at an operative orientation when said first contact surface is in abutting adjacency with said second contact surface, said first stop component being engageable with said first orientation boss when said positioning shaft is at said operative orientation, a first guideway within said retainer portion extending along said receiving cavity between said second contact surface and an inwardly disposed cam surface and having a widthwise extent for slideably receiving said first orientation boss in guiding relationship when said positioning shaft is inserted within said receiving cavity, said first lower cam follower surface being movable upon said second contact surface to locate said first orientation boss within said first guideway for movement therealong to a fully inserted orientation of said positioning shaft suited for subsequent rotational movement of said first orientation boss first upper cam follower surface upon said inwardly disposed cam surface to said operative orientation, a second guideway within said retainer portion extending along said receiving cavity between said second contact surface and said inwardly disposed cam surface and having a widthwise extent for slideably receiving said second orientation boss in guiding relationship when said positioning shaft is inserted within said receiving cavity, said second orientation boss being movable within said second guideway with said positioning shaft to said fully inserted orientation suited for subsequent rotational movement of said second upper cam follower surface upon said inwardly disposed cam surface simultaneously with said movement of said first upper cam follower surface upon said inwardly disposed cam surface, an electrical contact assemblage mounted within said handle housing adjacent said receiving cavity and having electrical contacts mounted thereon engageable in circuit completing relationship with said electrical terminal assemblage when said positioning shaft is in said operative orientation, a flexible electrical transmission cable coupled to said handle housing and having electrical leads connected with electrical contact assemblage electrical contacts and extending to an electrical connector component, a sealing assembly extending about said electrical contact assemblage and engageable in sealing relationship with said electrical contact assemblage and engageable in sealing relationship with said positioning shaft when in said operative orientation, and a signal treatment and control assembly having an input connector for removable electrical coupling with said cable electrical connector component and responsive to said output signals conveyed by said cable to provide perceptible output signals.

32. A surgical system for detecting and locating sources of radiation emission emanating from tissue of a body, comprising:

a sterilizable detector component, comprising:

a detector housing including a forward portion extending along a detector axis to a forward window through which said radiation emission is transmissible, and a support portion extending from said forward portion to a first contact surface and including a cylindrical positioning shaft extending a predetermined length outwardly from said support portion, said positioning shaft including a first orientation boss extending therefrom at a predetermined location, having a first widthwise extent, a first upper cam follower surface and an oppositely disposed first lower cam follower surface, a crystal mount positioned within said detector housing forward portion;

a crystal detector positioned upon said crystal mount, said detector having a forward surface adjacent said window and an oppositely disposed rearward surface and responsive to radiation passing through said window to provide a detector output, a treatment circuit within said detector housing, responsive to said detector output to provide output signals corresponding therewith, an electrical terminal assemblage mounted upon said positioning shaft and in electrical communication with said treatment circuit, a latching notch extending from said first contact surface of said detector housing support portion, a manually retractable latching component slideably mounted upon said handle housing at said retainer portion and spring biased for movement from a retracted position outwardly from said second contact surface into latching insertion within said latching notch when said positioning shaft is at said operative orientation;

a disposable handle component, including:

a hand gripable handle housing having a forwardly disposed second contact surface and a forwardly disposed retainer portion with a receiving cavity which includes a first guideway extending along said receiving cavity between said second contact surface and an inwardly disposed cam surface, said first guideway having a widthwise extent for slideably receiving said first orientation boss in guiding relationship when said positioning shaft is inserted within said receiving cavity, said receiving cavity configured for removably receiving said positioning shaft to locate it at an operative orientation, when said first contact surface is in abutting adjacency with said second contact surface, an electrical contact assemblage mounted within said handle housing adjacent said receiving cavity and having electrical contacts mounted thereon engageable in circuit completing relationship with said electrical terminal assemblage when said positioning shaft is in said operative orientation, a flexible electrical transmission cable coupled to said handle housing and having electrical leads connected with electrical contact assemblage electrical contacts and extending to an electrical connector component, a sealing assembly extending about said electrical contact assemblage and engageable in sealing relationship with said positioning shaft when in said operative orientation, and a signal treatment and control assembly having an input connector for removable electrical coupling with said cable electrical connector component and responsive to said output signals conveyed by said cable to provide perceptible output signals.

* * * * *